United States Patent [19]
Takasugi et al.

[11] Patent Number: 5,270,825
[45] Date of Patent: Dec. 14, 1993

[54] IMAGING OPTICAL SYSTEM HAVING A MOIRE ELIMINATION EFFECT

[75] Inventors: Yoshiharu Takasugi, Saitama; Akira Hasegawa, Tokyo, both of Japan

[73] Assignee: Olympus Optical Co., Ltd., Tokyo, Japan

[21] Appl. No.: 596,074

[22] Filed: Oct. 11, 1990

[30] Foreign Application Priority Data

Oct. 12, 1989 [JP] Japan ................................ 1-263867
May 2, 1990 [JP] Japan ................................ 2-115107

[51] Int. Cl.$^5$ ........................ H04N 5/30; H04N 5/225
[52] U.S. Cl. .................................... 358/209; 358/225; 358/98; 359/708
[58] Field of Search ...................... 358/50, 44, 43, 225, 358/209, 98; 350/432, 400, 401, 402, 404, 96.25, 96.26; 250/578.1, 227.20; 359/708

[56] References Cited

U.S. PATENT DOCUMENTS

| | | | |
|---|---|---|---|
| 3,787,609 | 1/1974 | Plumeau | 358/44 |
| 4,101,929 | 7/1978 | Ohneda et al. | 358/44 |
| 4,196,968 | 4/1980 | Itoh | 359/708 |
| 4,477,153 | 10/1984 | Suda | 359/708 |
| 4,575,193 | 3/1986 | Greivenkamp, Jr. | 358/55 |
| 4,605,956 | 8/1986 | Cok | 358/55 |
| 4,626,897 | 12/1986 | Sato et al. | 358/55 |
| 4,709,260 | 11/1987 | Geerts et al. | 358/225 |
| 4,720,178 | 1/1988 | Nishioka et al. | 358/98 |
| 4,720,637 | 1/1988 | Clark | 250/578 |
| 4,749,267 | 6/1988 | Mihara | 359/708 |
| 4,805,028 | 2/1989 | Nishioka et al. | 358/225 |
| 4,930,861 | 6/1990 | Okabe et al. | 350/96.25 |
| 4,977,450 | 12/1990 | Yokota | 358/55 |
| 5,007,719 | 4/1991 | Hasegawa | 350/425 |

FOREIGN PATENT DOCUMENTS

51-14033  5/1976  Japan .

*Primary Examiner*—Victor R. Kostak
*Assistant Examiner*—Sherrie Hsia
*Attorney, Agent, or Firm*—Cushman, Darby & Cushman

[57] ABSTRACT

An imaging optical system for forming images of objects on an image surface. The optical system includes an aspherical surface that functions to reduce spatial frequency response of the optical system when aperture size of the optical system is reduced within a variable range and adapted so as to eliminate spurious signal by the aspherical surface.

11 Claims, 24 Drawing Sheets

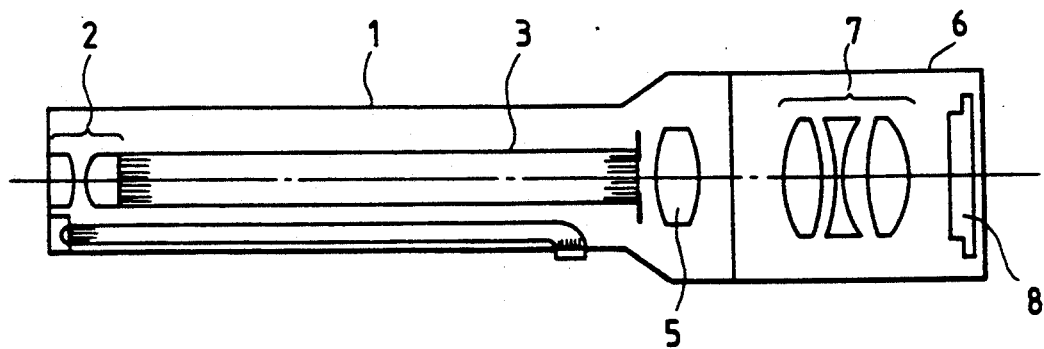
FIG. 4
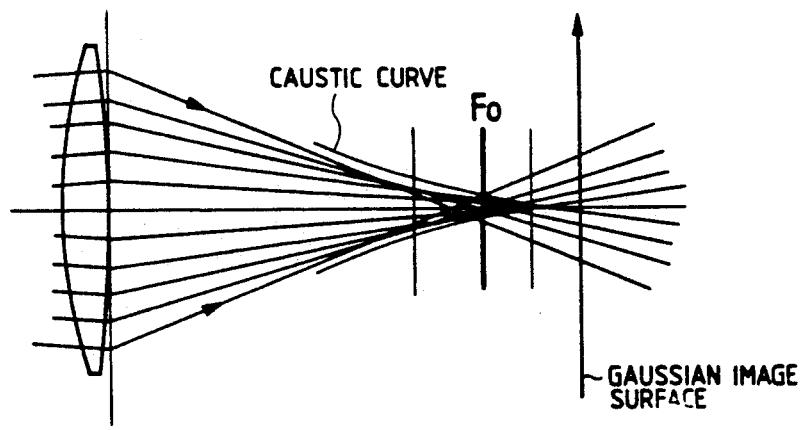
FIG. 5
FIG. 6A  FIG. 6B  FIG. 6C
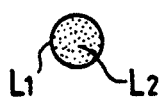  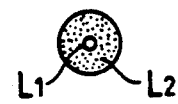

IMAGING OPTICAL SYSTEM HAVING A MOIRE ELIMINATION EFFECT

BACKGROUND OF THE INVENTION a) Field of the invention

The present invention relates to an imaging optical system to be used in television cameras, electronic still cameras, electronic endoscopes and so on.

b) Description of the prior art

In the optical instruments such as television cameras, electronic still cameras and electronic endoscopes, which are adapted so as to obtain colored images by using solid-state image pickup devices or image pickup tubes, image quality is degraded remarkably by spurious signals such as moiré and aliasing which are produced due to interference between the sampling frequency which are determined by arrangement of the picture elements in the solid-state image pickup devices and arrangement pitch of the filter elements in the color-coding filter array provided before the solid-state image pickup devices or image pickup tubes, and the spatial frequency components of the images of objects formed on the light receiving surfaces of the solid-state image pickup devices or image pickup tubes.

As a conventional imaging optical system adapted so as to eliminate the spurious signals, there is known the optical system disclosed by Japanese Patent Kokoku Publication No. Sho 51-14033 (U.S. Pat. No. 4,720,637). This imaging optical system comprises an optical low-pass filter composed of a birefringent plate such as calcite.

When imaging condition is changed in photographing an object having a large value at a specific spatial frequency, however, the imaging optical system comprising the optical low-pass filter can not eliminate the spurious signals sufficiently or at all. This defect becomes especially remarkable when a television camera is attached to an eyepiece lens of a fiber scope or when a photograph printed in dots is photographed with a television camera. This imaging optical system will be described detailedly below taking an example wherein the imaging optical system is used in a fiber scope.

A condition where a television camera is attached to the eyepiece of a fiber scope is schematically shown in FIG. 1, wherein a television camera 7 comprising an photographic lens 4, an optical low-pass filter 5 and an image pickup device 6 such as CCD is attached to a fiber scope 3 comprising an image guide fiber bundle 1 and an eyepiece lens 2 so that an image formed on the end surface of emergence of the image guide fiber bundle 1 is focused on the light receiving surface of the image pickup device 6 by the eyepiece lens 2 and the photographic lens 4.

The image guide fiber bundle is composed, as is known well to those skilled in the art, of a large number of optical fibers bundled densely in hexagonal sectional shape. On the end surface of emergence of the image guide fiber bundle, only cores 8 of the fibers arranged regularly as shown on an enlarged scale in FIG. 2 are bright. Accordingly, an image of the end surface of emergence can be considered as an arrangement of the bright spots of the cores 8 which is modulated by distribution of brightness on the object. A spatial frequency spectrum of the image of the end surface of emergence of the image guide fiber bundle has an intense spectrum component at the fundamental frequency determined dependently on arrangement of the cores. The spurious signals are produced due to the interference between the fundamental frequency and the sampling frequency of the CCD 6, and are eliminated insufficiently when the image is photographed with a television camera to which various types of fiber scopes are attached.

FIG. 3A and FIG. 3B show sectional views illustrating a portion of the imaging optical system composed by attaching a television camera to an eyepiece lens of a fiber scope. In these drawings, the reference numeral 1 represents an image guide fiber bundle of the fiber scope, the reference numeral 2 designates an eyepiece lens, the reference numeral 14 (14') denotes an exit pupil of the eyepiece lens, the reference numeral 4 represents a photographic lens of the television camera and the reference numeral 6 designates an image pickup device. An image of object appearing on the end surface of emergence of the image guide fiber bundle 1 is focused on the image pickup device 6 by an imaging optical system consisting of the eyepiece lens 2 and the photographic lens 4. Since NA of each of the rays emerging from the fibers of the image guide fiber bundle 1 of the fiber scope is constant, F number of the imaging optical system is deterimined by the eyepiece lens 4 and size of the exit pupil 14 (14').

Thickness of fiber scopes is various, i.e., thick or thin, dependently on purposes of application. Further, thickness of image guide fiber bundles used in fiber scopes is also various. However, the visual fields visible through eyepiece lenses should have areas which are the substantially the same for convenience of observation. For this reason, eyepiece lenses have various magnifications, i.e., eyepiece lenses provided for thin image guide fiber bundles have high magnifications, whereas eyepiece lenses adopted for thick image guide fiber bundles have low magnifications. In order to observe images through these different fiber scopes at brightness levels which are the substantially the same, diameter of the exit pupil 14 is enlarged so as to thicken the light bundle incident on the photographic lens 4 when the eyepiece lens has a low magnification (or a long focal length) as shown in FIG. 3A, whereas diameter of the exit pupil 14' is reduced so as to thin the light bundle incident on the photographic lens 4 when the eyepiece lens 2 has a high magnification as shown in FIG. 3B since the NA of each of the rays emerging from the optical fibers is constant. Accordingly, the photographic lens 4 has a small F number when the eyepiece lens 2 has a low magnification or a large F number when the eyepiece lens 2 has a high magnification.

Now, let us assume that the optical fibers composing the image guide have the same diameter, that the optical fibers are arranged at a pitch of p, that the eyepiece lens having the low magnification and the photographic lens have a total magnification of $\beta_L$, and that the eyepiece lens having the high magnification and the photographic lens have a total magnification of $\beta_H$. Then, mesh-like patterns formed by the optical fibers of the image guide are projected to the light receiving surface of the image pickup device at a high frequency of $1/(p\beta_L)$ in the case where the eyepiece lens having the low magnification is used, whereas the patterns are projected at a low frequency of $1/(p\beta_H)$ in the case where the eye-piece lens having the high magnification is used. Accordingly, the fundamental frequency of an image of object is high when an image formed by an endoscope equipped with the eyepiece lens having the low magnification is photographed, i.e., when the imaging optical system has a large F number, whereas the fundamental frequency of an image of object is low when an image formed by an endoscope equipped with the eyepiece lens having the high magnification is photographed, i.e., when the imaging optical system has a small F number.

The optical low pass filter prevents the interference between the spatial frequency components of an image of object and the sampling frequency of an image pickup device by lowering resolution of the image at frequencies higher than a specific spatial frequency. When MTF (Modulation Transfer Function) is taken as the ordinate and spatial frequency is taken as the abscissa, the optical low pass filter has such a frequency response as shown by the solid line in FIG. 12. As is seen from the frequency response curve shown in FIG. 12, it is possible to obtain an effect to eliminate the spurious signals in the imaging optical system having a small F number by using an optical low pass filter which is composed so as to zero MTF at the fundamental frequency $1/(p\ \beta_L)$ (the point A in FIG. 12) of the imaging optical system having the small F number. However, it is impossible to lower resolution and eliminate the spurious signals by using the optical low pass filter having the composition described above in the imaging optical system having a large F number since the MTF has a large value at the fundamental frequency $1/(p\ \beta_M)$ (the point B in FIG. 12) of the imaging optical system having the large F number. When a low pass filter which zeroes the MTF at the frequency $1/(p\ \beta_M)$ is used in the imaging optical system having the large F number so that the spurious signals can be eliminated in the imaging optical system having the large F number, the MTF has a small value at the frequency $1/(p\ \beta_H)$ though it should desirably have large values at the frequencies lower than $1/(p\ \beta_L)$ and resolution is becomes lower than required, thereby degrading image quality.

As is understood from the foregoing description, the conventional imaging optical system using the optical low pass filter poses various problems for eliminating the spurious signals when the optical system is used for imaging an object which has a large spectrum component at a specific spatial frequency.

Certain imaging optical systems utilize defocusing as a means to eliminate the spurious signals such as moiré. Speaking concretely, the spurious signals are eliminated by defocusing images with the imaging optical systems set so as to deviate the image surfaces a little from the optimum positions thereof. When the images are defocused for eliminating the spurious signals at such a degree as to lower the spatial frequency response of the image pickup device to the Nyguist frequency or the spatial frequency response of the image guide fiber bundle to the fundamental frequency described above, it is possible to suppress the high order spectra produced due to the images of the regular arrangement on the end surface of emergence of the image guide and eliminate moiré by sampling the images having transmitted through the optical fibers for individual picture elements of the image pickup device.

However, since the ordinary optical systems have rather high response even within the region of high frequencies, the images must be defocused at high degrees for reducing the spatial frequency components and the defocusing of the images linearly lowers the MTF curve as the spatial frequency becomes higher. Accordingly, selection of a low cut-off frequency for elimination of moiré results in lowering of response at the frequencies lower than the cut-off frequency and degradation of resolution. Further, moiré is not eliminated sufficiently when a measure is taken to prevent resolution from being degraded.

Furthermore, it is necessary to determine degrees of the defocusing in conjunction with apertures of endoscopes to be used with the imaging optical system.

SUMMARY OF THE INVENTION

A primary object of the present invention is to provide an imaging optical system which is effectively usable with endoscopes of types different from one another and equipped with a means for eliminating the spurious signals without degrading resolving power of the optical system.

Another object of the present invention is to provide an imaging optical system which is capable of always providing images of good qualities free from moiré regardless of variation of aperture size.

A further object of the present invention is to provide an imaging optical system which uses an aspherical surface as an optical means for eliminating the spurious signals.

A further object of the present invention is to provide an imaging optical system which uses, as an optical means for eliminating the spurious signals, an aspherical surface having at least two inflection points within a range of variation of aperture size.

A further object of the present invention is to provide an imaging optical system comprising a zoom optical system and an aspherical surface which serves for eliminating the spurious signals and located on the object side of a variator arranged in the zoom optical system.

The imaging optical system according to the present invention is to be attached to an eyepiece lens of an endoscope for focusing an image covering a specific frequency range such as an image formed on the end surface of emergence of an image guide on an image pickup device, and uses an optical means which has a curve of a specific aberration, especially spherical aberration, having a shape varying with variation of aperture size and functioning to vary light intensity distribution on a spot image along with the variation of aperture size so as to lower the spatial frequency response when aperture size is small.

FIG. 4 shows a schematic sectional view illustrating an imaging unit which uses the imaging optical system according to the present invention and adapted in such a manner that an image transmitted through an image guide and formed on the end surface of emergence thereof is focused on the light receiving surface of an image pickup device. In this drawing, an image of an object is formed on the end surface of incidence of an image guide fiber bundle 3 by an objective lens 2 of a fiber scope 1. The image transmitted through the image guide fiber bundle 3 and formed on the surface of emergence thereof is enlarged by an eyepiece lens 5 for observation usually by a naked eye. In order to focus the image formed by the fiber scope 1 onto the light receiving surface of the image pickup device 8 of the imaging system 6, an imaging lens sysetm 7 is attached to the fiber scope 1.

Since optical fibers are arranged densely and regularly in a hexagonal sectional shape in the image guide fiber bundle of the endoscope as described above, the spurious signals such as moiré are produced in the imaging unit.

Description will be made on the means adopted for eliminating these spurious signals by producing a specific aberration in the imaging optical system.

There is available an imaging means generally called "soft focus lens" which formes a defocused image by producing a specific aberration, especially spherical aberration, in an optical system.

The spherical aberration exits in both the axial and offaxial regions, and has a characteristic that it is produced symmetrically with regard to the optical axis. When the spherical aberration is produced in an optical system, the aberration (only the spherical aberration of the third order will be considered for simplicity) is generally in such a condition as shown in FIG. 5. On an image surface located in the vicinity of the Gaussian image surface, the caustic curves form a circle $L_1$ and the light bundle forms a disk-like image $L_2$ as shown in FIG. 6A. Diameter of the light bundle (circle of confusion) is minimized by bringing the image surface to a location where the size of the circle $L_1$ is equal to that of the image $L_2$. The surface on which the light bundle has the minimum diameter is the optimum image surface and the light bundle has a larger diameter when the image surface deviates even little from that surface. This applies to both the conditions shown in FIG. 5 wherein the spherical aberration is undercorrected and in FIG. 7 wherein the spherical aberrations are overcorrected. In cases where the spherical aberrations of higher orders, i.e., the fifth order and the seventh order, are included, the shape of the caustic curves and the condition of the spherical aberration become different or more complicated, but the diameter of the light bundle varies fundamentally in the same manner as in the case illustrated in FIG. 5.

An aperture size of an imaging optical system to be attached to an eyepiece lens of an endoscope is ordinarily determined dependently on stop diameter of the eyepiece lens. An eyepiece lens having a high magnification is generally selected for a fiber scope which has a small aperture size. Therefore, the specific spatial frequency determined by structure of the optical fiber bundle is low on the image surface. Accordingly, it is required to defocus an image at a high degree by the imaging optical system for lowering MTF or remarkably defocus the image on the optimum image surface. In case of a fiber scope having a large aperture size, in contrast, an eyepiece lens having a high magnification and a high specific spatial frequency is selected, whereby an image is defocused at a low degree by the imaging optical system for lowering MTF at this high frequency.

As is understood from the foregoing description, it is necessary to defocus an image at a high degree or enlarge the circle of confusion on the image surface for the imaging optical system to be used with a fiber scope having a small aperture size, whereas defocusing of an image at a low degree or a small circle of confusion is sufficient for the imaging optical system to be used with a fiber scope having a large aperture size.

Though the image surface is defocused as a whole and the spurious signals are eliminated in an endoscope, it must have resolution of a certain degree. Further, it is necessary to lower the spatial frequency response of the imaging optical system to a certain degree when it is combined with a fiber scope having a small aperture size, whereas it is desirable not to degrade the characteristic of the imaging optical system so much when it is combined with a fiber scope having a large aperture size.

In an imaging optical system which has a spherical aberration curve of the ordinary shape as shown in FIG. 8, the aberration is produced in a larger amount at a larger aperture size, i.e., at higher height of ray. Accordingly, this imaging optical system lowers resolution more than required since the spatial frequency response thereof is lowered more remarkably at a large aperture size than at a small aperture size.

In an imaging optical system having such a spherical aberration as shown in FIG. 9, the aberration is maximum at a certain aperture size of a. When this imaging optical system is used with a fiber scope having a large aperture size, the rays passing through an aperture which is larger than the size a produce little aberration. Comparison of a case where this imaging optical system with a fiber scope having an aperture size on the order of a with another case where the imaging optical system is used with another fiber scope having an aperture size larger than a will clarify that the amount of the rays which emerge from an optional point on an object, pass through the portions of an aperture and are converged in the vicinity of an ideal image point is smaller than that of the rays which emerge from the same point on the object, pass through the portions of the aperture and are converged on marginal portion apart from the ideal image point in both the cases, but the difference is larger in the former case than in the latter case. As is understood from this fact, the imaging optical system having the spherical aberration shown in FIG. 9 less degrades the spatial frequency responce and provides a better characteristic when used with a fiber scope having a large aperture size than that available when the imaging optical system is used with a fiber scope having a small aperture size. That is to say, it is necessary to design the imaging optical system so as to have such an aberration characteristic that the spherical aberration is produced in the largest amount when the imaging optical system is used with a fiber scope which has the smallest aperture size out of the various types of fiber scopes to be used actually therewith, and that the aberration is produced in amounts as little as possible when the imaging optical system is used with the fiber scopes having larger aperture sizes.

The present invention eliminates the spurious signals by producing the spherical aberration in the imaging optical system, varying the approximate shape of the curve of the spherical aberration dependently on aperture size so as to vary intensity distribution on a spot image, and lowering the spatial frequency response for images having small aperture sizes as described above.

It is desirable for the imaging optical system according to the present invention that it has the spherical aberration of a certain degree at small aperture sizes but that it has sufficiently corrected spherical aberration at large aperture sizes.

Generally speaking, the spherical aberration produced by positive lenses is undercorrected and monotonously increases as rays becomes higher.

FIG. 8 shows a curve illustrating spherical aberration of the third order produced by a positive lens which also produces spherical aberration of the higher orders actually. When it is desired to modify a spherical aberration curve of this positive lens so as to have a desired shape, it is necessary to vary the spherical aberration of the fifth order and the seventh order. In order to vary the spherical aberration with no influence on the aberrations other than the spherical aberration, it is preferable to use not only spherical lenses but also aspherical lenses in optical systems.

Generally, the spherical aberration is produced in a larger amount as rays passing through the optical systems are higher and the focal lengths of the optical systems are shorter. This is because the rays incident on the positive lens are refracted more largely as the lens portions are farther from the optical axis toward the marginal portion thereof. In order to increase spherical aberration produced at a certain height of ray, it is therefore sufficient to refract the ray at that height more largely. Refracting function of a lens surface for a ray at a certain height can be enhanced by reducing the radius of curvature on the surface, but the reduction of the radius of curvature will vary spherical aberrations at the other heights. In order to obtain the spherical aberrations of desired amounts at all the heights, it is preferable to use an aspherical surface. In other words, use of an aspherical surface facilitates to produce the spherical aberration of higher orders than that produced by a spherical surface. Further, an attempt made to produce the spherical aberration of high orders only with spherical lenses will remarkably vary a composition of a lens system as a whole and shapes of the lens elements comprised therein, thereby making it difficult to manufacture the lens elements in practice and correct the other aberrations.

The enhancement of refracting function mentioned above menas strengthening the converging function of a positive lens or the diverging function of a negative lens, i.e., increasing the positive power of a positive lens or the negative power of a negative lens.

As described above, amount of spherical aberration to be produced is related to focal lengths of optical systems, and refracting functions of lens elements, as well as departure from reference sphere at each height of ray when an aspherical surface is used. Departure $\Delta z$ from a reference sphere at a height of ray Ia on an aspherical surface is taken as positive when the aspherical surface deviates from the reference sphere in the travelling direction of the ray, or negative when the aspherical surface is deviated in the reverse direction. However, powers of lens elements may be different for departures having the same sign. The aspherical surface illustrated in FIG. 10, for example, has a negative departure and its power is weakened at the marginal portion thereof. In contrast, the aspherical surface shown in FIG. 11 has a negative departure but its power is strengthened at the marginal portion. That is to say, power of a lens element may vary in different ways, even at the same departure from a reference sphere (or even when $\Delta z$ has the same sign), dependently on whether an aspherical surface is arranged on the object side or the image side of the lens element, and whether the reference sphere has a concave surface or a convex surface on the object side.

Shapes of aspherical surfaces are generally expressed by the following formula:

$$z = \frac{Cy^2}{1 + \sqrt{1 - pC^2y^2}} + By^2 + Ey^4 + Fy^6 + \ldots$$

wherein the optical axis is taken as the z axis, the direction toward the image is taken as positive, the intersection between the aspherical surface and the optical axis is taken as the origin, and the direction perpendicular to the optical axis is taken as the y axis. Further, the reference symbol C represents the inverse number of the radius of curvature on the reference sphere, the reference symbol p designates the conical coefficient, and the reference symbols B, E, F, ... denote the aspherical surface coefficients of the second, fourth, sixth, ... orders. The formula mentioned above expresses an spherical surface when $p=1$ and all of B, E, F, ... are zero.

When the imaging optical system according to the present invention uses an aspherical surface, it is desirable to design the aspherical surface so as to satisfy the following condition (1):

(1) $1 \times 10^{-5} |\Delta z|/f < 5 \times 10^{-2}$ wherein the reference symbol $\Delta z$ represents the departure from the reference sphere at the height of the marginal ray passing through said aspherical surface at the maximum aperture size, and the reference symbol f designates the focal length of the iamging optical system as a whole.

The spherical aberration is produced generally in a larger amount as height of ray becomes larger as described above. It is necessary in the imaging optical system according to the present invention to suppress the spherical aberration at large aperture sizes, i.e., at large heights of rays.

If the lower limit of the condition (1) is exceeded, the spherical aberration will not be corrected sufficiently by the aspherical surface. If the upper limit of the condition (1) is exceeded, in contrast, the spherical aberration will undesirably be overcorrected.

Description will be made on the imaging performance of the imaging optical system which has the spatial frequency response described above.

An imaged condition of an image point on the image surface of the imaging optical system is schematically illustrated in FIG. 13 wherein aperture size is taken as the ordinate, distance as measured in the direction perpendicular to the optical axis is taken as the abscissa and the imaged condition is represented as the lateral aberration. In addition, the reference symbol $\Delta A$ designates a range within which aperture size varies.

In order to lower the cut-off frequency of MTF as the aperture has a smaller size and enhance the cut-off frequency of MTF as the aperture has a larger size, it is necessary that diameter $\phi_A$ of a circle of confusion at an optional aperture size within the range $\Delta A$ wherein aperture size is variable is smaller than diameter $\phi_{min}$ of circle of confusion at the minimum aperture size. That is to say, the following relationship must be established between $\phi_A$ and $\phi_{min}$:

$$\phi_{min} > \phi_A$$

In this case, the diameters of the circle of confusion are as illustrated in FIG. 14A, FIG. 14B and FIG. 14C. In these drawings, profile of intensity distributions on spot images are shown taking intensity on the spot images is taken as the ordinate and distance as measured from the optical axis on a plane perpendicular to the optical axis as the abscissa. Out of these drawings, FIG. 14A shows an intensity distribution when the stop has the minimum aperture size, FIG. 14B illustrates an intensity distribution when the stop has an intermediate aperture size and FIG. 14C visualizes an intensity distribution when the stop has the maximum aperture size.

Since the imaging optical system has a lateral aberration which is constant to the minimum aperture size as seen from FIG. 13, the profile of intensity distribution on the spot image is a cylinder having a diameter equal to the value $\phi_{min}$ of the lateral aberration as shown in FIG. 14A. When aperture size becomes larger than the minimum value thereof, the light bundle corresponding to the lateral aberration $\phi_A$ has a larger diameter, whereby the profile of the intensity distribution on the spot image has a shape including a protrusion produced by the component having the diameter $\phi_A$ and the circle of confusion has a diameter smaller than $\phi_{min}$ as shown in FIG. 14B. When the aperture size becomes maximum, the light bundle corresponding to the lateral aberration $\phi_A$ has the largest diameter, whereby the profile of intensity distribution on the spot image has a higher protrusion having the diameter $\phi_A$ and the circle of confusion has a smaller diameter which is close to $\phi_A$ as shown in FIG. 14C.

It is practically difficult to design the imaging optical system so that the lateral aberration has a value which is completely constant within a certain range of aperture sizes. Accordingly, the intensity distribution on the spot image or imaged condition is varied so as to vary the outside diameter thereof not stepwise as shown in FIG. 14B and FIG. 14C, but continuously vary the outside diameter of the profile. However, the discussion made above is sufficient for conceptional examination and comprehending the characteristics of optical systems.

Now, the imaging characteristic described above will be examined from the viewpoint of the spatial frequency by using the special function defined in "Introduction to Fourier Optics" written by J. Doodman.

The characteristic visualized in FIG. 14A through FIG. 14C is a cylinder having a height of 1 and a diameter of $\phi_{min}$ which is traced in two dimensions. A function expressing this shape is called "cylinder function (cyl (x))" and defined by using a two-dimensional polar coordinates as follows:

$$\text{cyl}(r/d) = \begin{cases} 1 & (0 \leq r < d/2) \\ 1/2 & (r = d/2) \\ 0 & (d/2 < r) \end{cases}$$

wherein the reference symbol r represents distance as measured from the origin.

By using the function mentioned above, the shape illustrated in FIG. 14A can be expressed as follows:

$$\text{cyl}(r/\phi_{min}) \qquad (i)$$

Fourier transformation of this function gives the spatial frequency response. By using the polar coordinates, Fourier transformation of a function which is revolutionally symmetrical on the two-dimensional coordinates is transformed into Hankel transformation. Relationship between an iptional function f(r) and Hankel transformation thereof F(p) is given by the following formula (ii):

$$\left. \begin{array}{l} F(\rho) = 2\pi \int_0^\infty f(r') J_0(2\pi\rho r') r' dr' \\ f(r) = 2\pi \int_0^\infty F(\rho') J_0(2\pi r\rho') d\rho' \end{array} \right\} \qquad (ii)$$

wherein the reference symbol $J_0(2\pi r\rho^1)$ represents Bessel function of the 0 order.

Further, Hankel transformation of the cylinder function expressed by the formula (i) can be expressed as the following formula (iii) by using a sombrero function (somb (x)):

$$(\pi\phi_{min}^2/4) \text{ somb}(\phi_{min}\rho) \qquad (iii)$$

wherein the sombrero function is defined as follows:

$$\text{somb}(r/d) = \frac{2J_1\{(\pi/d)r\}}{(\pi/d)r}$$

wherein $J_1\{(\pi/d)r\}$ is Bessel function of the first order.

The formula (iii) expresses MTF of the imaging optical system exhibiting the intensity distribution on spot image as shown in FIG. 14A and the cut-off frequency (the first zero point) $\rho_{min}$ thereof is as expressed below:

$$\rho_{min} = 1.22/\phi_{min}$$

wherein the reference symbol $\rho$ represents the distance as measured from the origin on the frequency plane, i.e., the spatial frequency.

Then, the shape illustrated in FIG. 14C is, when viewed in two dimensions, equal to the shape shown in FIG. 15A and that shown in FIG. 15B which are overlapped with each other.

When the image height in FIG. 15A is taken as 1 and that in FIG. 15B is taken as a for convenience of calculations, the intensity distribution on spot image illustrated in FIG. 15C can be expressed by the following formula:

$$f(r) = \text{Cyl}(r/\phi_{min}) + a \text{ cyl}(r/\phi_A)$$

Hankel transformation of the second term of the above-mentioned formula gives the following result:

$$(\pi a\phi_A^2/4) \text{ somb}(\phi_A\rho)$$

The imaging optical system having the intensity distribution illustrated in FIG. 14C has a cut-off frequency of $\phi = 1.22/\phi_A$.

Hence, Hankel transformation of f(r), i.e., MTF of the imaging optical system having the intensity distribution on spot image, is given by the following formula (iv):

$$F(\rho) = \pi/4 \{\phi_{min}^2 \text{somb}(\phi_{min}\rho) + a\phi_A^2 \text{somb}(\phi_A\rho)\} \qquad (iv)$$

Since the coefficients of the sombrero function somb ($\phi_A$) represent the volumes of the cylinders illustrated in FIG. 15A and FIG. 15B respectively, a ratio between these coefficients is expressed by the following formula (V):

$$A = a\phi_A/\phi_{min}^2 \qquad (v)$$

By dividing both the terms of the formula (v) by a constant $K = \pi\phi_{min}^2/4$ which is not varied by changing aperture size, we obtain the following formula (vi):

$$\frac{1}{K} \cdot F(\rho) = \text{somb}(\phi_{min}\rho) + A \text{ somb}(\phi_A \rho) \quad \text{(vi)}$$

Value of a used in the formula (v) expressing the coefficient A is determined by an area of an aperture. In FIG. 16, the reference numerals 15 and 16 represent a minimum aperture and a maximum aperture within a variable range of aperture sizes and the reference symbol R designates the diameter of the maximum aperture normalized to the diameter of the minimum aperture 15. Then, the formula (v) is transformed into the following formula (viii):

$$A = \phi_A/\phi_{min}(R^2-1) \quad \text{(vii)}$$

By using the formula (vii) in the formula (vi), we obtain the following formula (viii):

$$(1/K) \cdot F(\rho) = \text{somb}(\phi_{min}\rho) + (\phi_A/\phi_{min})(R^2-1)\text{somb}(\phi_A\rho) \quad \text{(viii)}$$

The second term of the formula (viii) has a larger value as R is enlarged. Accordingly, when R is equal to 1 or has the minimum value thereof, $(1/K) F(\rho)$ is expressed by the first term of the right side of the formula (viii) and the MTF of the imaging optical system is traced as a gently-sloping curve having a cut-off frequency $\rho = 1.22/\phi_{min}$. When aperture size is enlarged, however, the second term of the formula (viii) is added, the MTF is not zero at the frequency $\rho = 1.22/\phi_{min}$ and the second term has the following:

$$(\phi_A/\phi_{min})(R^2-1)\text{somb}\{1.22(\phi_A/\phi_{min})\}$$

Since the value of the second term is rapidly increased as R is enlarged, $\rho = 1.22/\phi_{min}$ is the cut-off frequency at large aperture sizes.

On the other hand, the value of the sombrero function is rapidly reduced from the first zero point toward the higher frequencies. Due to the nature inherent in Bessel function, $\rho = 1.22/\phi_A$ becomes the cut-off frequency in the substantial sense of the term.

In the MTF characteristic given by the formula (viii), the value of MTF at the first cut-off frequency $\rho = 1.22/\phi_{min}$ is progressively increased and $\rho = 1.22/\phi_A$ clearly appears as a new cut-off frequency in place of the above-mentioned cut-off frequency as aperture size of the stop changes from the minimum value thereof to the maximum value thereof. That is to say, the cut-off frequency changes dependently on aperture sizes.

Now, description will be made on a concrete means for obtaining an imaging optical system having the MTF characteristic described above.

The present invention imparts the MTF characteristic described above to the imaging optical system by producing the above-described specific spherical aberration in the optical system.

FIG. 17A and FIG. 17B show the spherical aberrations to be produced for imparting the MTF characteristic to the imaging optical system. Each of the spherical aberrations shown in FIG. 17A and FIG. 17B has a large swelling at small aperture sizes and another swelling at large aperture sizes, and is substantially the same as that illustrated in FIG. 13.

The spherical aberration shown in FIG. 17A will be compared with that illustrated in FIG. 17B. The imaging optical system having the spherical aberration can have the desired MTF characteristic in the vicinity of Gaussian image surface, whereas the imaging optical system having the spherical aberration illustrated in FIG. 17B can have the desired MTF characteristic when it is defocused for a definite distance from the Gaussian image surface.

FIG. 18 illustrates relationship between the MTF characteristic and defocused degree of the imaging optical systems described above. In FIG. 18, MTF is taken as the ordinate, defocused degree is taken as the abscissa, the solid line a and the chain line b correspond to the optical systems illustrated in FIG. 17A and FIG. 17B respectively. Both the optical systems having the spherical aberrations of the types shown in FIG. 17A and FIG. 17B have the desired values of MTF respectively at the best image surfaces thereof. In the optical system having the spherical aberration of the type shown in FIG. 17B, however, the rays incident on the image surface are eccentric with regard to the optical axis and the MTF of this optical system abruptly lowers when its image surface is apart from the best image surface. Accordingly, the imaging optical system has an MTF characteristic which is easily degraded by defocusing. On the other hand, the imaging optical system having the spherical aberration of the type shown in FIG. 17A has an MTF characteristic which is stable. Moreover, the imaging optical system having the spherical aberration of the type shown in FIG. 17A can easily be realized in practice by using an aspherical surface in the optical system.

Though no particular restriction is imposed on the imaging optical system in the foregoing description, it is preferable, in a case where the imaging optical system is designed as a vari-focal lens system such as a zoom lens system, to produce the spherical aberration on the incidence side of a lens unit having a vari-focal function.

FIG. 19 illustrates a vari-focal lens system of the front stop type having an exit pupil thereof at the foremost location. In FIG. 19, the reference numeral 9 represents a fixed lens unit or a compensator lens unit, the reference numeral 10 designates a variator lens unit, the reference numeral 12 denotes a compensator lens unit or a fixed lens unit, and the reference numeral 17 represents an optical low pass filter composed of a quartz plate.

When the fixed lens unit 9 is designed so as to produce the desired spherical aberration in this lens system, amount of the spherical aberration varies along with the variation of imaging magnification by the variator lens unit 10, thereby making it possible to eliminate moiré effectively regardless of zooming.

Further, since the lens system illustrated in FIG. 19 comprises the quartz plate 17, it is capable of eliminating moiré by utilizing both the spherical aberration and the characteristic of the quartz plate 17. When two means for eliminating moiré are combined as described above, it is desirable to select such an MTF characteristics as shown in FIG. 20. In this drawing, the solid line a indicates the MTF of the quartz plate 17. This quartz plate has no influence on defocusing and is free from degradation of MTF at low frequencies. However, the MTF of this quartz plate is enhanced again at high frequencies, thereby making elimination of the moiré stripes insufficient. Further, the MTF of the spherical aberration (the chain line 6) can be suppressed to a sufficiently low level at the high frequencies but has a defect that it is varied by defocusing especially at the high frequencies. It is possible to cancel these defects with each other by combining the quartz plate having the characteristic described above with the spherical aberration for elimination of the moiré stripes. By combining the quartz plate with the spherical aberration so as to satisfy the following condition, it is possible to obtain an MTF characteristic which is suited for elimination of the moiré stripes, free from variation due to defocusing, allows little degradation of resolution at the low frequencies and is sufficiently suppressed at low levels at the high frequencies:

$$\nu_c < \nu_M$$

wherein the reference symbols $\nu_c$ and $\nu_M$ represent the cut-off frequencies of the spherical aberration and the quartz plate respectively.

In addition, the dashed line C in FIG. 20 indicates the MTF characteristic obtained by combining the quartz plate and the spherical aberration.

BRIEF DESCRIPTION OF THE DRAWINGS

FIG. 4 shows a sectional view illustrating a composition of an imaging system equipped with the imaging optical system according to the present invention;

FIG. 5 shows a sectional view illustrating a converged condition of a light bundle in an optical system having undercorrected spherical aberration;

FIG. 6A, FIG. 6B and FIG. 6C show diagrams illustrating circles of confusion of the optical system shown in FIG. 5;

DETAILED DESCRIPTION OF THE PREFERRED EMBODIMENTS

Figure 1:
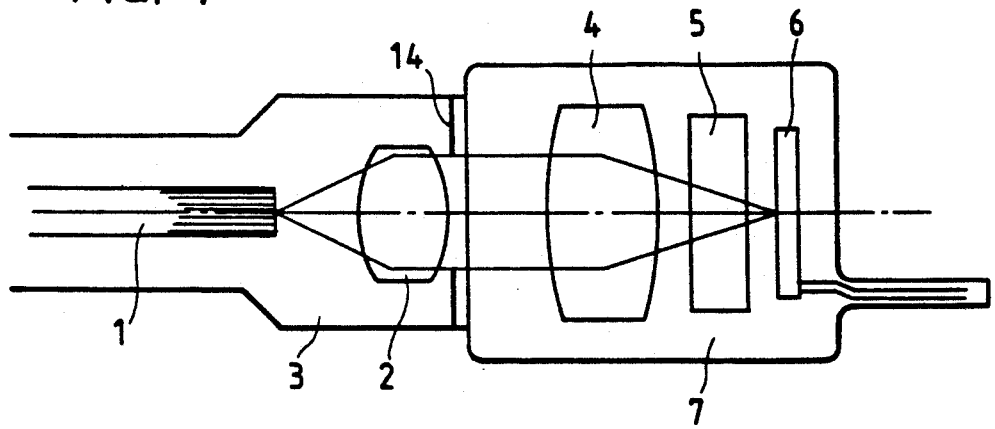
FIG. 1 shows a schematic sectional view illustrating a composition of a fiber scope combined with a television camera.
Figure 2:
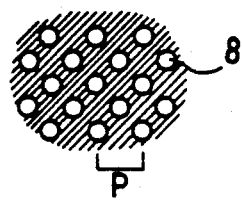
FIG. 2 shows a diagram illustrating an end surface of an image guide.
Figure 3A:
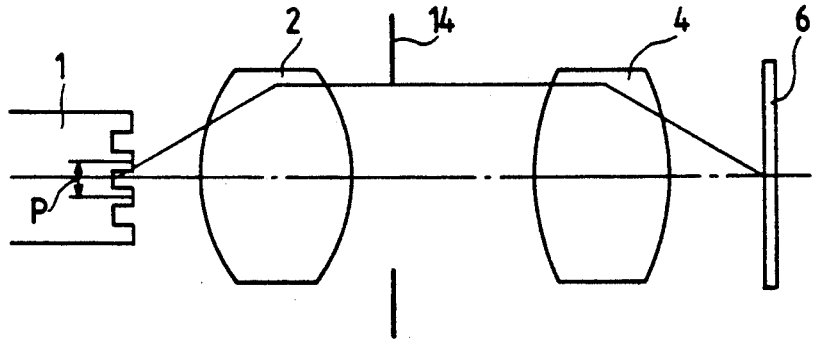
FIG. 3A and FIG. 3B show sectional views illustrating the composition of the conventional imaging optical system.
Figure 3B:
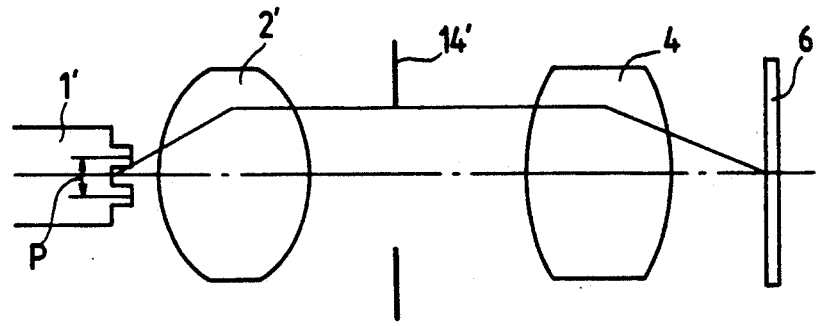
Figure 7:
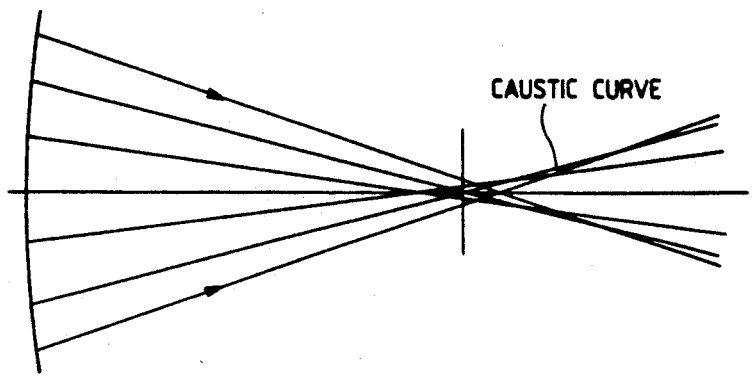
FIG. 7 shows a diagram illustrating a converged condition of rays in an optical system having overcorrected spherical aberration.
Figure 8:
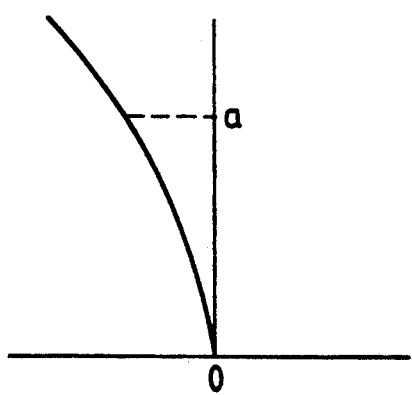
FIG. 8 and FIG. 9 graphs exemplifying spherical aberration curves respectively.
Figure 9:
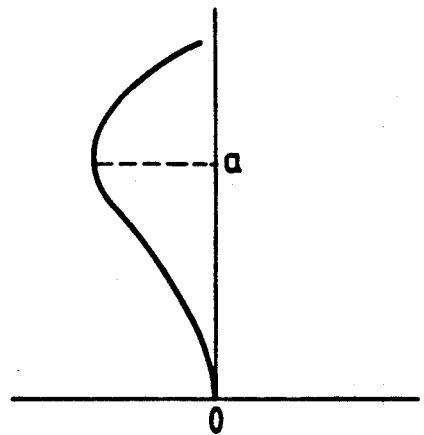
Figure 10:
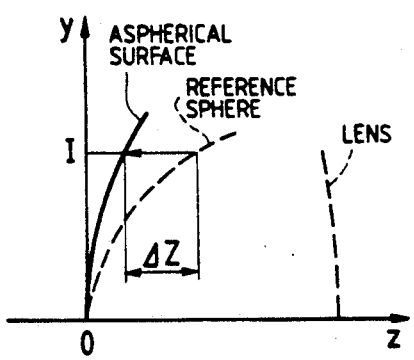
FIG. 10 and FIG. 11 show graphs illustrating relationship between aspherical surfaces and the reference spheres thereof.
Figure 11:
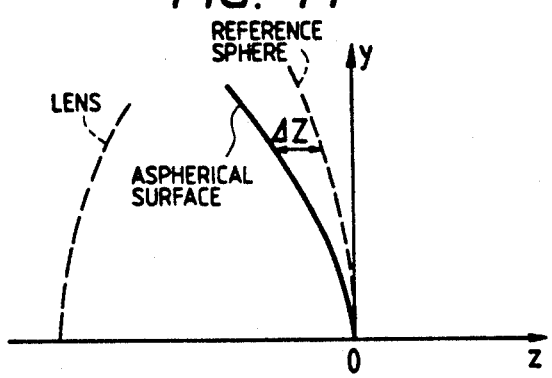
Figure 12:
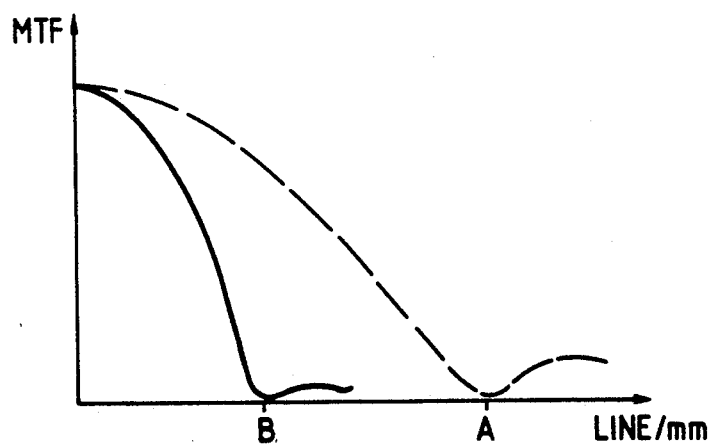
FIG. 12 shows graphs illustrating MTF's of the conventional optial systems.
Figure 13:
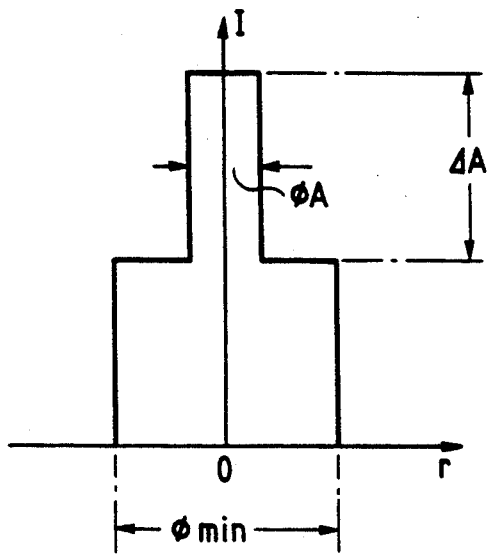
FIG. 13, FIG. 14A, FIG. 14B, FIG. 14C, FIG. 15A and FIG. 15B show diagrams illustrating relationship between aperture sizes of optical systems and lateral aberration on spot images.
Figure 14A:
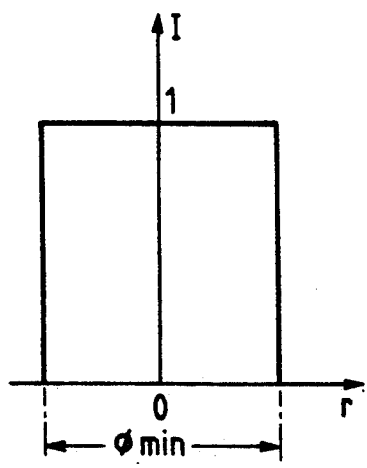
Figure 14B:
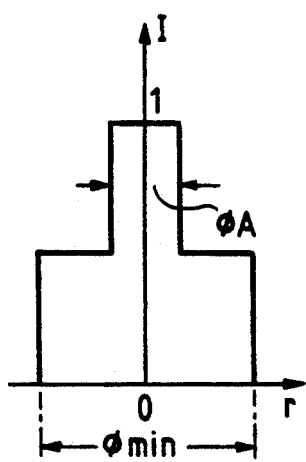
Figure 14C:
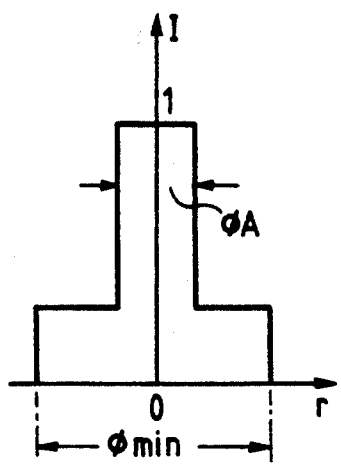
Figure 15A:
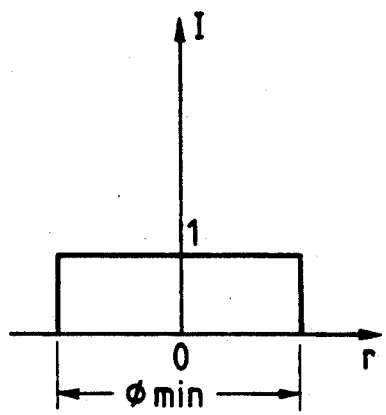
Figure 15B:
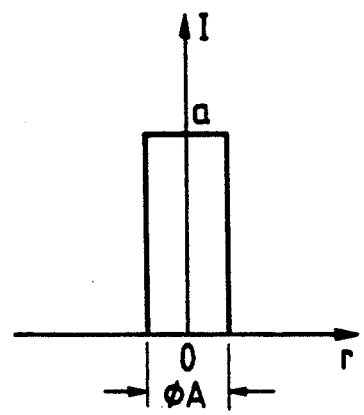
Figure 16:
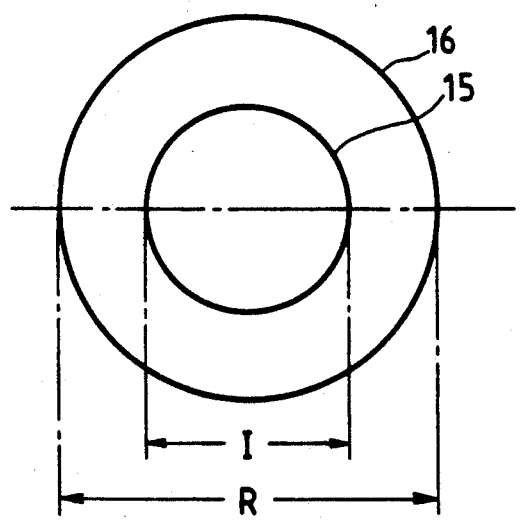
FIG. 16 shows a diagram illustrating variation of an aperture of a light bundle.
Figure 17A:
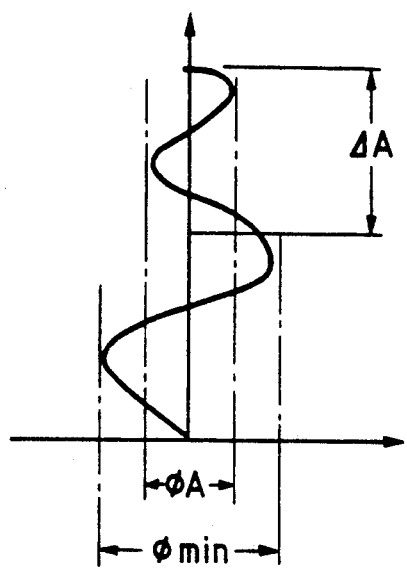
FIG. 17A and FIG. 17B show graphs exemplifying the spherical aberration in the imaging optical system according to the present invention.
Figure 17B:
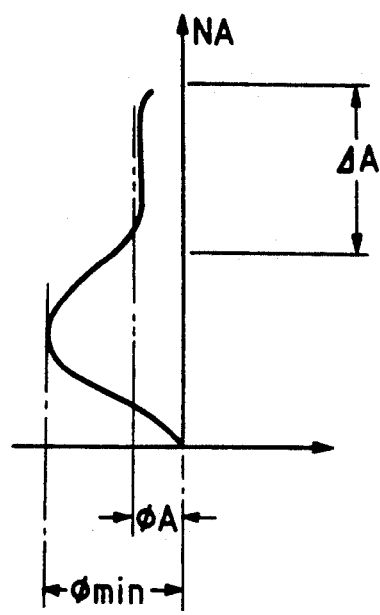
Figure 18:
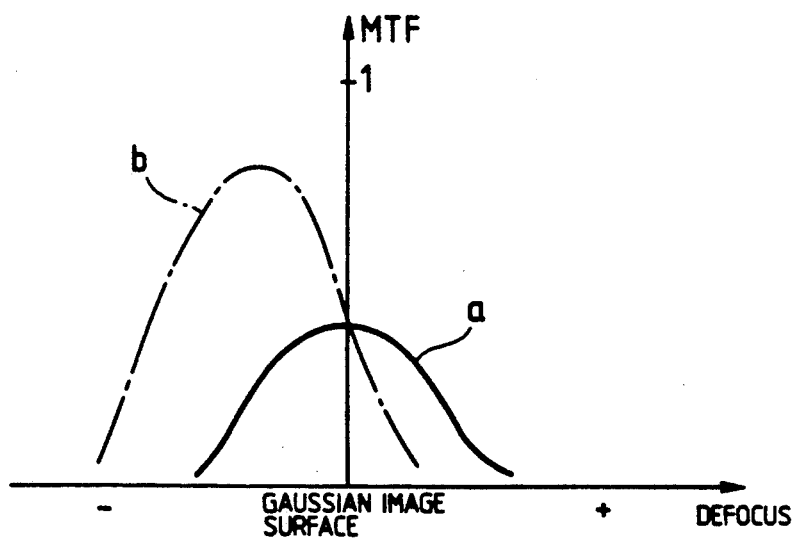
FIG. 18 shows graphs illustrating relationship between defocused degrees and MTF's.

Now, the imaging optical system according to the present invention will be described with reference to the preferred Embodiments shown in the accompanying drawings and given in the form of the following numerical data:

Embodiment 1
f = 1.000   F/5.3   2ω = 12.966°
             IH = 0.112
$r_1 = \infty$ (stop)
  $d_1 = 0.0101$
$r_2 = \infty$
  $d_2 = 0.0338$   $n_1 = 1.51633$   $\nu_1 = 64.15$
$r_3 = \infty$
  $d_3 = 0.1387$
$r_4 = \infty$ -continued

|  |  |  |  |
|---|---|---|---|
| $r_5 = \infty$ | $d_4 = 0.0274$ | $n_2 = 1.51633$ | $\nu_2 = 64.15$ |
|  | $d_5 = 0.0947$ |  |  |
| $r_6 = -0.5160$ (aspherical surface) |  |  |  |
|  | $d_6 = 0.0338$ | $n_3 = 1.65160$ | $\nu_3 = 58.52$ |
| $r_7 = 0.2372$ |  |  |  |
|  | $d_7 = 0.0609$ | $n_4 = 1.71736$ | $\nu_4 = 29.51$ |
| $r_8 = 0.4516$ |  |  |  |
|  | $d_8 = 0.1827$ |  |  |
| $r_9 = 1.7262$ |  |  |  |
|  | $d_9 = 0.1218$ | $n_5 = 1.73400$ | $\nu_5 = 51.49$ |
| $r_{10} = -0.5382$ |  |  |  |
|  | $d_{10} = 0.0169$ |  |  |
| $r_{11} = -51.7006$ |  |  |  |
|  | $d_{11} = 0.1691$ | $n_6 = 1.74400$ | $\nu_6 = 44.73$ |
| $r_{12} = -0.2970$ |  |  |  |
|  | $d_{12} = 0.0440$ | $n_7 = 1.78472$ | $\nu_7 = 25.71$ |
| $r_{13} = -1.4354$ |  |  |  |
|  | $d_{13} = 0.0271$ |  |  |
| $r_{14} = \infty$ |  |  |  |
|  | $d_{14} = 0.0605$ | $n_8 = 1.51633$ | $\nu_8 = 64.15$ |
| $r_{15} = \infty$ |  |  |  | aspherical coefficient
$P = 1.0000, \quad B = 0.10209$
$E = 0.29207 \times 10, \quad F = -0.18885 \times 10^3$
$\Delta Z = 0.000948$ Embodiment 2
$f = 1.0000 \quad F/14.2 \quad 2\omega = 7.92°$
$IH = 0.071$

|  |  |  |  |
|---|---|---|---|
| $r_1 = \infty$ (stop) | $d_1 = 0.0072$ |  |  |
| $r_2 = \infty$ | $d_2 = 0.0362$ | $n_1 = 1.51633$ | $\nu_1 = 64.15$ |
| $r_3 = \infty$ | $d_3 = 0.1183$ |  |  |
| $r_4 = 0.2077$ (aspherical surface) |  |  |  |
|  | $d_4 = 0.0821$ | $n_2 = 1.71300$ | $\nu_2 = 53.84$ |
| $r_5 = -2.3524$ | $d_5 = 0.0644$ |  |  |
| $r_6 = -0.3082$ | $d_6 = 0.0532$ | $n_3 = 1.75520$ | $\nu_3 = 27.51$ |
| $r_7 = 0.1928$ | $d_7 = 0.1193$ |  |  |
| $r_8 = 0.7072$ | $d_8 = 0.0687$ | $n_4 = 1.59270$ | $\nu_4 = 35.29$ |
| $r_9 = -0.4648$ | $d_9 = 0.1132$ |  |  |
| $r_{10} = \infty$ | $d_{10} = 0.0362$ | $n_5 = 1.51633$ | $\nu_5 = 64.15$ |
| $r_{11} = \infty$ |  |  |  | aspherical coefficient
$P = 1.0000, \quad B = -0.14089$
$E = 0.55469 \times 10, \quad F = -0.37135 \times 10^4$
$\Delta Z = -0.000185$ Embodiment 3
$f = 1.000 \quad F/14.2 \quad 2\omega = 7.92°$
$IH = 0.071$

|  |  |  |  |
|---|---|---|---|
| $r_1 = \infty$ (stop) | $d_1 = 0.0072$ |  |  |
| $r_2 = \infty$ | $d_2 = 0.0361$ | $n_1 = 1.51633$ | $\nu_1 = 64.15$ |
| $r_3 = \infty$ | $d_3 = 0.1182$ |  |  |
| $r_4 = 0.2124$ (aspherical surface) |  |  |  |
|  | $d_4 = 0.0820$ | $n_2 = 1.71300$ | $\nu_2 = 53.84$ |
| $r_5 = -3.1152$ | $d_5 = 0.0643$ |  |  |
| $r_6 = -0.2677$ | $d_6 = 0.0531$ | $n_3 = 1.75520$ | $\nu_3 = 27.51$ |
| $r_7 = 0.1876$ | $d_7 = 0.1192$ |  |  |
| $r_8 = 0.7285$ | $d_8 = 0.0687$ | $n_4 = 1.59270$ | $\nu_4 = 35.29$ |
| $r_9 = -0.4113$ | $d_9 = 0.1131$ |  |  |
| $r_{10} = \infty$ | $d_{10} = 0.0361$ | $n_5 = 1.51633$ | $\nu_5 = 64.15$ |
| $r_{11} = \infty$ |  |  |  | aspherical coefficient
$P = 1.0000, \quad B = 0.38924 \times 10^{-1}$
$E = -0.53838 \times 10, \quad F = 0.37115 \times 10^4$
$\Delta Z = 0.000050$ Embodiment 4
$f = 1.0000 \quad F/2.1 \quad 2\omega = 13°$
$IH = 0.113$

|  |  |  |  |
|---|---|---|---|
| $r_1 = \infty$ (stop) | $d_1 = 0.0263$ |  |  |
| $r_2 = \infty$ | $d_2 = 0.0876$ | $n_1 = 1.51633$ | $\nu_1 = 64.15$ |
| $r_3 = \infty$ | $d_3 = 0.1927$ |  |  |
| $r_4 = \infty$ | $d_4 = 0.0876$ | $n_2 = 1.51633$ | $\nu_2 = 64.15$ |
| $r_5 = \infty$ | $d_5 = 0.0964$ |  |  |
| $r_6 = 0.6745$ (aspherical surface) |  |  |  |
|  | $d_6 = 0.1734$ | $n_3 = 1.78590$ | $\nu_3 = 44.18$ |
| $r_7 = 5.9213$ | $d_7 = 0.0436$ |  |  |
| $r_8 = -1.1230$ | $d_8 = 0.0701$ | $n_4 = 1.78472$ | $\nu_4 = 25.71$ |
| $r_9 = 0.6375$ | $d_9 = 0.0816$ |  |  |
| $r_{10} = 3.4100$ | $d_{10} = 0.1165$ | $n_5 = 1.88300$ | $\nu_5 = 40.78$ |
| $r_{11} = -1.1935$ | $d_{11} = 0.0392$ |  |  |
| $r_{12} = 3.1698$ | $d_{12} = 0.0788$ | $n_6 = 1.69680$ | $\nu_6 = 55.52$ |
| $r_{13} = -1.4952$ | $d_{13} = 0.2134$ |  |  |
| $r_{14} = \infty$ | $d_{14} = 0.0964$ | $n_7 = 1.52000$ | $\nu_7 = 74.00$ |
| $r_{15} = \infty$ | $d_{15} = 0.0175$ |  |  |
| $r_{16} = \infty$ | $d_{16} = 0.1209$ | $n_8 = 1.54869$ | $\nu_8 = 45.55$ |
| $r_{17} = \infty$ | $d_{17} = 0.1577$ | $n_9 = 1.54869$ | $\nu_9 = 45.55$ |
| $r_{18} = \infty$ | $d_{18} = 0.1323$ | $n_{10} = 1.54869$ | $\nu_{10} = 45.55$ |
| $r_{19} = \infty$ | $d_{19} = 0.0175$ |  |  |
| $r_{20} = \infty$ | $d_{20} = 0.3153$ | $n_{11} = 1.80610$ | $\nu_{11} = 40.95$ |
| $r_{21} = \infty$ | $d_{21} = 0.0350$ | $n_{12} = 1.51633$ | $\nu_{12} = 64.15$ |
| $r_{22} = \infty$ |  |  |  | aspherical coefficient
$P = 1.0000, \quad B = 0.76013 \times 10^{-1}$
$E = 0.35469, \quad F = 0.63098$
$\Delta Z = 0.005588$ Embodiment 5
$f = 1.000 \quad F/2.1 \quad 2\omega = 13.01°$
$IH = 0.113$

|  |  |  |  |
|---|---|---|---|
| $r_1 = \infty$ (stop) | $d_1 = 0.0263$ |  |  |
| $r_2 = \infty$ | $d_2 = 0.0876$ | $n_1 = 1.51633$ | $\nu_1 = 64.15$ |
| $r_3 = \infty$ | $d_3 = 0.1926$ |  |  |
| $r_4 = \infty$ | $d_4 = 0.0876$ | $n_2 = 1.51633$ | $\nu_2 = 64.15$ |
| $r_5 = \infty$ | $d_5 = 0.0963$ |  |  |
| $r_6 = 0.7068$ (aspherical surface) |  |  |  |
|  | $d_6 = 0.1734$ | $n_3 = 1.78590$ | $\nu_3 = 44.18$ |
| $r_7 = 5.8596$ | $d_7 = 0.0438$ |  |  |
| $r_8 = -1.6385$ | $d_8 = 0.0700$ | $n_4 = 1.78470$ | $\nu_4 = 26.22$ |
| $r_9 = 0.7826$ | $d_9 = 0.0832$ |  |  |
| $r_{10} = 2.8652$ | $d_{10} = 0.1165$ | $n_5 = 1.88300$ | $\nu_5 = 40.78$ |
| $r_{11} = -1.2074$ | $d_{11} = 0.0394$ |  |  |
| $r_{12} = -7.6465$ | $d_{12} = 0.0788$ | $n_6 = 1.70154$ | $\nu_6 = 41.24$ |
| $r_{13} = -1.2684$ | $d_{13} = 0.2097$ |  |  |
| $r_{14} = \infty$ | $d_{14} = 0.0963$ | $n_7 = 1.52000$ | $\nu_7 = 74.00$ |
| $r_{15} = \infty$ |  |  |  |

-continued

|  |  |  |  |
|---|---|---|---|
| $r_{16} = \infty$ | $d_{15} = 0.0175$ | | |
| | $d_{16} = 0.4106$ | $n_8 = 1.54869$ | $\nu_8 = 45.55$ |
| $r_{17} = \infty$ | $d_{17} = 0.0175$ | | |
| $r_{18} = \infty$ | $d_{18} = 0.3152$ | $n_9 = 1.80610$ | $\nu_9 = 40.95$ |
| $r_{19} = \infty$ | $d_{19} = 0.0350$ | $n_{10} = 1.51633$ | $\nu_{10} = 64.15$ |
| $r_{20} = \infty$ | | | | aspherical coefficient
P = 1.0000,   E = −0.30802
F = 0.16161 × 10
ΔZ = −0.000698

Embodiment 6 f = 1.000    F/2.1    2ω = 12.978°
IH = 0.113

|  |  |  |  |
|---|---|---|---|
| $r_1 = \infty$ (stop) | $d_1 = 0.0263$ | | |
| $r_2 = \infty$ | $d_2 = 0.0876$ | $n_1 = 1.51633$ | $\nu_1 = 64.15$ |
| $r_3 = \infty$ | $d_3 = 0.1926$ | | |
| $r_4 = \infty$ | $d_4 = 0.0876$ | $n_2 = 1.51633$ | $\nu_2 = 64.15$ |
| $r_5 = \infty$ | $d_5 = 0.0963$ | | |
| $r_6 = 0.6241$ | $d_6 = 0.1734$ | $n_3 = 1.78590$ | $\nu_3 = 44.18$ |
| $r_7 = -1.9996$ | $d_7 = 0.0438$ | | |
| $r_8 = -0.8841$ | $d_8 = 0.0700$ | $n_4 = 1.78472$ | $\nu_4 = 25.71$ |
| $r_9 = 0.6177$ | $d_9 = 0.0832$ | | |
| $r_{10} = -5.4879$ | $d_{10} = 0.1165$ | $n_5 = 1.88300$ | $\nu_5 = 40.78$ |
| $r_{11} = -1.0629$ | $d_{11} = 0.0394$ | | |
| $r_{12} = -29.7088$ | $d_{12} = 0.0787$ | $n_6 = 1.69700$ | $\nu_6 = 48.51$ |
| $r_{13} = -0.9127$ | | | |

Embodiment 7 f = 18.285 (wide position), 28.252 (tele position)
F/3.457 (wide position), F/5.125 (tele position)

|  |  |  |  |
|---|---|---|---|
| $r_1 = \infty$ | $d_1 = 0.3000$ | | |
| $r_2 = \infty$ | $d_2 = 1.0000$ | $n_1 = 1.51633$ | $\nu_1 = 64.15$ |
| $r_3 = \infty$ | $d_3 = 3.5000$ | | |
| $r_4 = \infty$ | $d_4 = 1.0000$ | $n_2 = 1.51633$ | $\nu_2 = 64.15$ |
| $r_5 = \infty$ | $d_5 = 3.2000$ | | |
| $r_6 = \infty$ | $d_6 = 9.0000$ | $n_3 = 1.79952$ | $\nu_3 = 42.24$ |
| $r_7 = \infty$ | $d_7 = D_1$ (variable) | | |
| $r_8 = 9.0310$ (aspherical surface) | $d_8 = 3.0700$ | $n_4 = 1.51633$ | $\nu_4 = 64.15$ |
| $r_9 = 25.3350$ | $d_9 = D_2$ (variable) | | |
| $r_{10} = \infty$ | $d_{10} = 7.4600$ | $n_5 = 1.54869$ | $\nu_5 = 45.55$ |
| $r_{11} = \infty$ | $d_{11} = 1.2000$ | | |
| $r_{12} = -8.6190$ | $d_{12} = 0.8000$ | $n_6 = 1.88300$ | $\nu_6 = 40.78$ |
| $r_{13} = 16.9840$ | $d_{13} = D_3$ (variable) | | |
| $r_{14} = \infty$ | $d_{14} = 3.0000$ | $n_7 = 1.69680$ | $\nu_7 = 55.52$ |
| $r_{15} = -10.1010$ | $d_{15} = 0.2000$ | | |
| $r_{16} = 30.5000$ | $d_{16} = 2.5000$ | $n_8 = 1.51633$ | $\nu_8 = 64.15$ |
| $r_{17} = -267.8860$ | $d_{17} = 0.2000$ | | |
| $r_{18} = 9.8350$ | $d_{18} = 4.0000$ | $n_9 = 1.69680$ | $\nu_9 = 55.52$ |
| $r_{19} = \infty$ | | | |
| $r_{20} = 17.4010$ | $d_{19} = 0.9700$ | $n_{10} = 1.84666$ | $\nu_{10} = 23.78$ |
| | $d_{20} = 2.2000$ | | |
| $r_{21} = \infty$ | $d_{21} = 6.5000$ | $n_{11} = 1.54869$ | $\nu_{11} = 45.55$ |
| $r_{22} = \infty$ | | | | aspherical coefficient
P = 0.9833,    E = 0.23958 × 10⁻², B = 0
F = −0.28856 × 10⁻², G = 0.13786 × 10⁻²
H = −0.33695 × 10⁻³, I = 0.44546 × 10⁻⁴
J = −0.30277 × 10⁻⁵, K = 0.82796 × 10⁻⁷

| | wide position | tele position |
|---|---|---|
| $D_1$ | 1.100 | 1.100 |
| $D_2$ | 1.000 | 3.540 |
| $D_3$ | 3.340 | 0.800 | wherein the reference symbols $r_1$, $r_2$, ... represent the radii of curvature on the surfaces of the respective lens elements, the reference symbols $d_1$, $d_2$, ... designate the thicknesses of the respective lens elements and the airspaces reserved therebetween, the reference symbols $n_1$, $n_2$, ... denote the refractive indices of the respective lens elements, and the reference symbols $\nu_1$, $\nu_2$, ... represent the Abbe's numbers of the respective lens elements.

Figure 21:
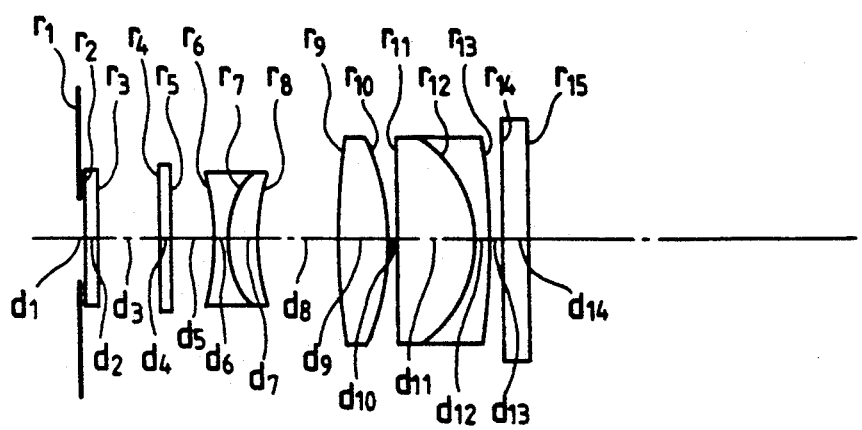
FIG. 21 through FIG. 26 show sectional views illustrating compositions of Embodiments 1 through 6 of the imaging optical system according to the present invention.

The Embodiment 1 is an imaging optical system composed of a negative lens unit and a positive lens unit as shown in FIG. 21. In the optical system preferred as the Embodiment 1, the first surface ($r_6$) of the negative lens unit is designed as an aspherical surface which produces spherical aberration. In this optical system, spherical aberration is produced more remarkably by higher rays. Further, the aspherical surface is arranged at a location close to an aperture stop in the Embodiment 1 so as to make rays symmetrical and produce astigmatism as little as possible. In other words, remarkable astigmatism or curvature of field will enlarge the circle of confusion on the image surface, thereby making it impossible to obtain the moir/e,acu/e/ eliminating effect and high resolution even when the spherical aberration curve has an adequate shape.

Figure 28:
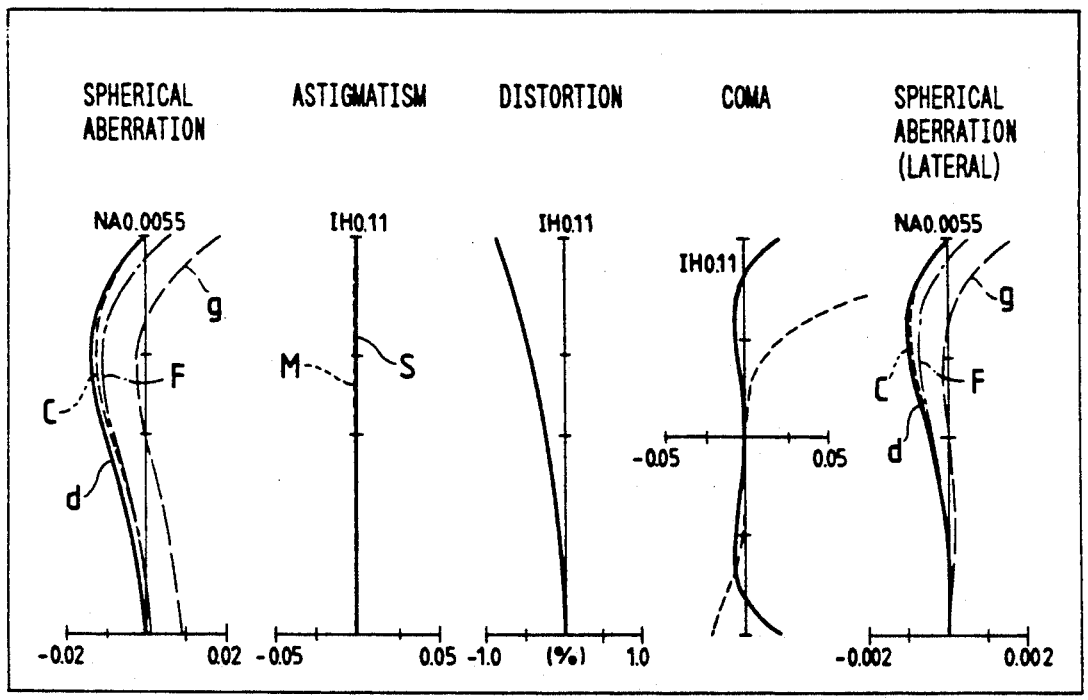
FIG. 28 through FIG. 33 show curves illustrating aberration characteristics of the Embodiments 1 through 6 of the present invention.

Aberration characteristics of the Embodiment 1 are illustrated in FIG. 28, wherein the spherical aberration is zeroed at the maximum aperture size and the maximum at an aperture ratio of approximately 0.7.

Figure 22:
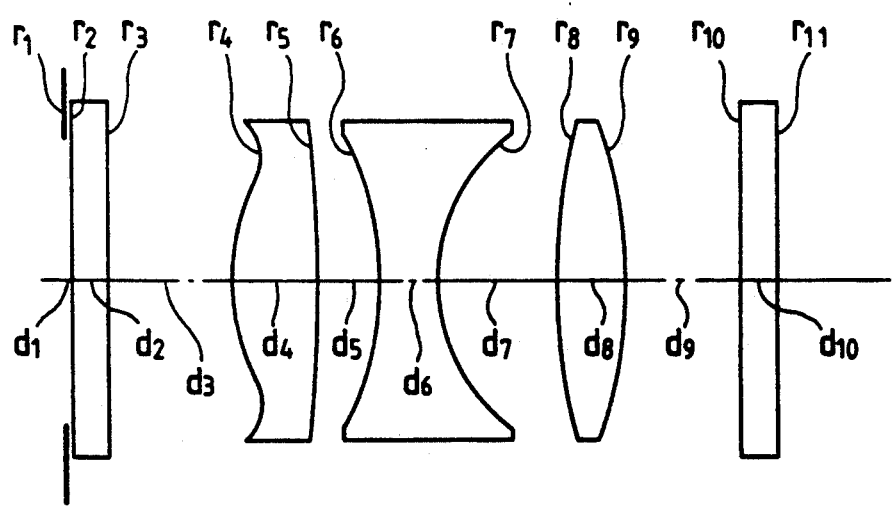
Figure 23:
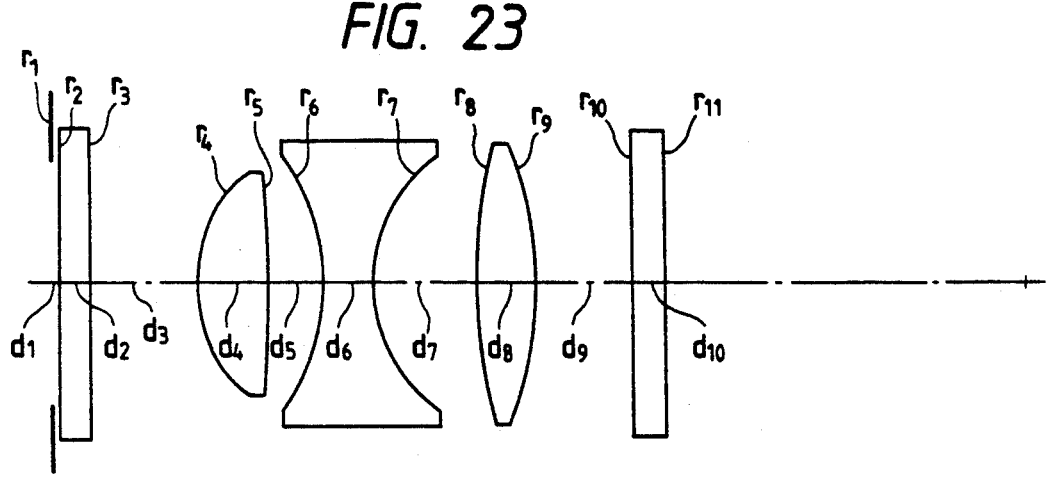

The Embodiments 2 and 3 have the compositions illustrated in FIG. 22 and FIG. 23 respectively, and each of the imaging optical systems is designed as a triplet type consisting of a positive lens unit, a negative lens unit and a positive lens unit.

Figure 29:
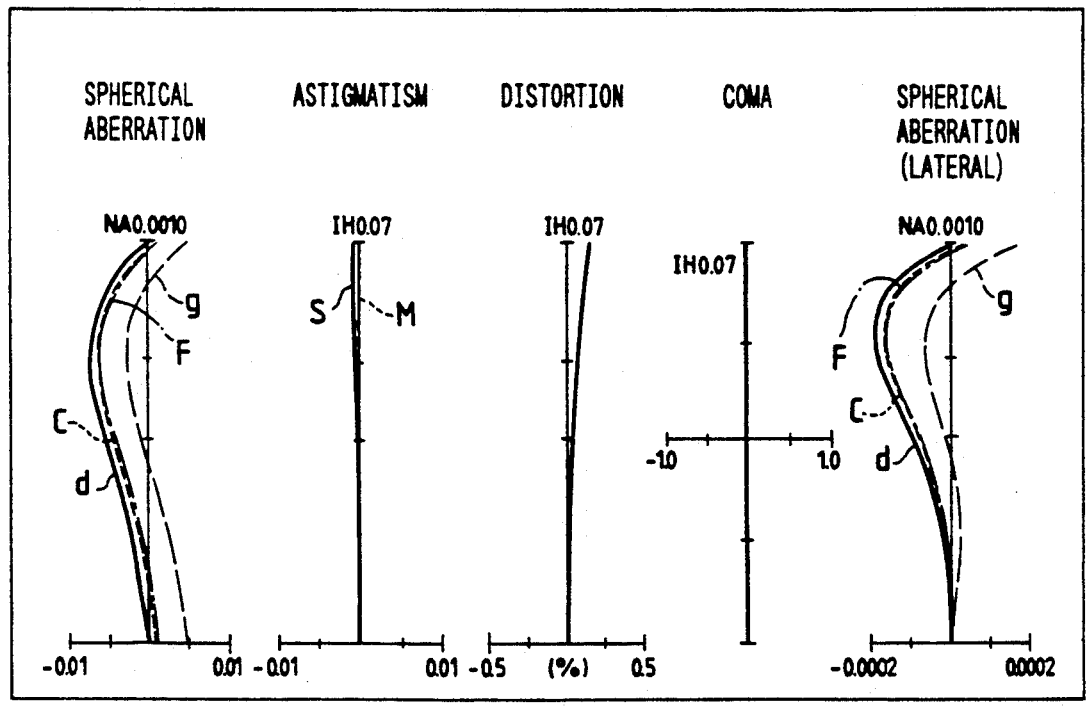

The Embodiment 2 has an aspherical surface as the first surface ($r_4$) of the optical system. This aspherical surface has a shape whose curvature is progressively lowered as the surface portions are farther from the optical axis. Aberration characteristics of the Embodiment 2 are illustrated in FIG. 29 wherein spherical aberration is produced on the negative side.

Figure 30:
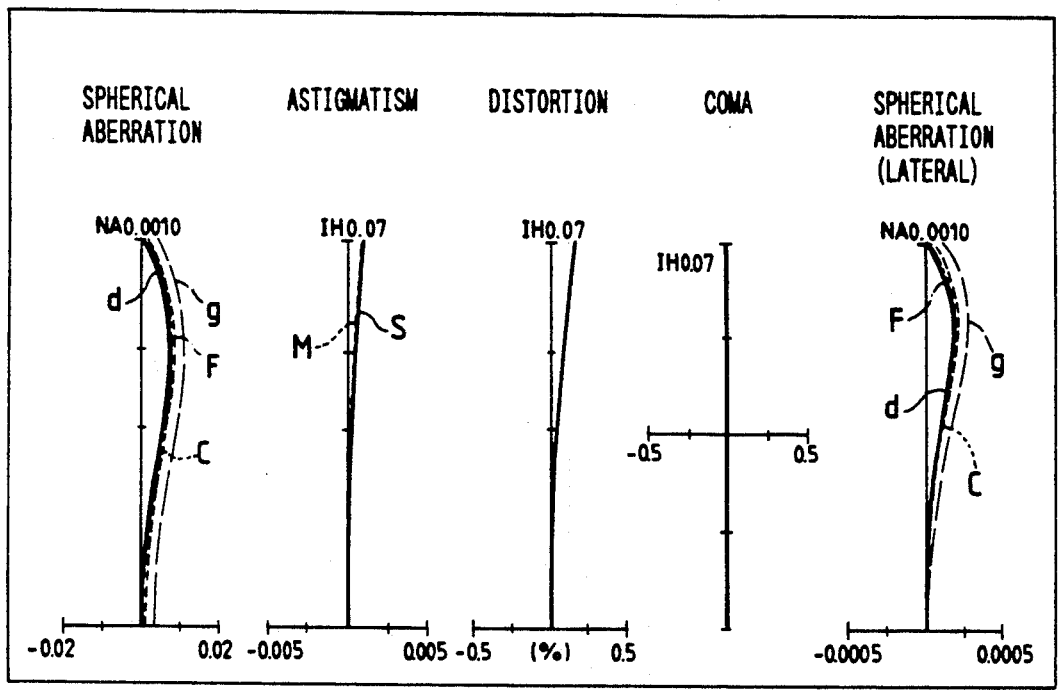

The Embodiment 3 has the composition which is similar to that of the Embodiment 2 but uses an aspherical surface whose curvature is progressively enhanced as the surface portions are farther from the optical axis, reversely to the curvature of the aspherical surface adopted in the Embodiment 2. Aberration characteristics of the Embodiment 3 are visualized in FIG. 30 wherein spherical aberration is produced on the positive side.

Figure 24:
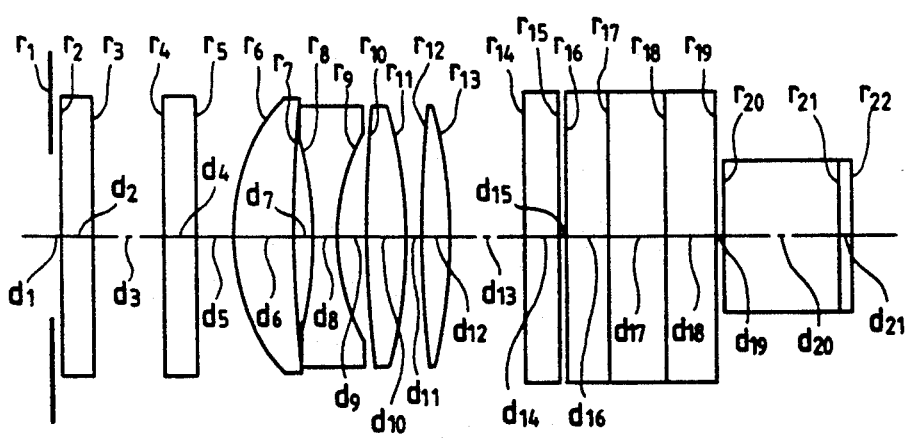
Figure 25:
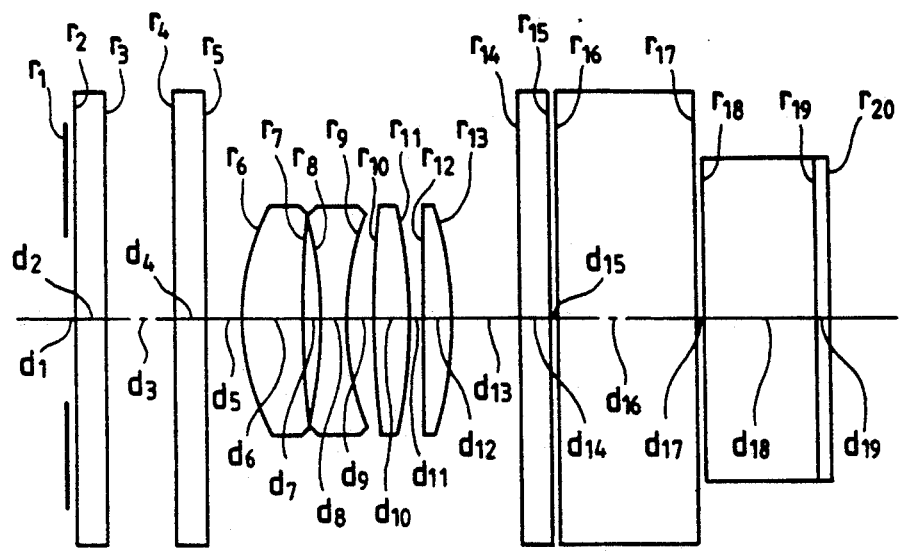

The Embodiments 4 and 5 have the compositions illustrated in FIG. 24 and FIG. 25 respectively, and each of the imaging optical system is composed of a positive lens unit, a negative lens unit and a positive lens unit, and adopts an aspherical surface as the first surface ($r_6$) thereof.

Figure 31:
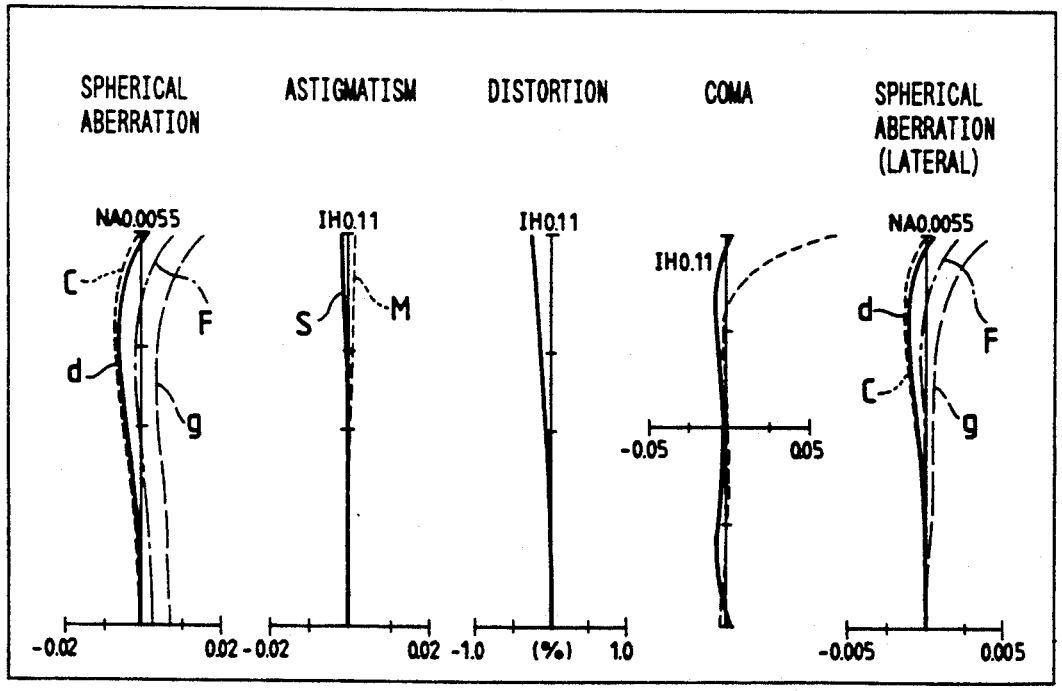
Figure 32:
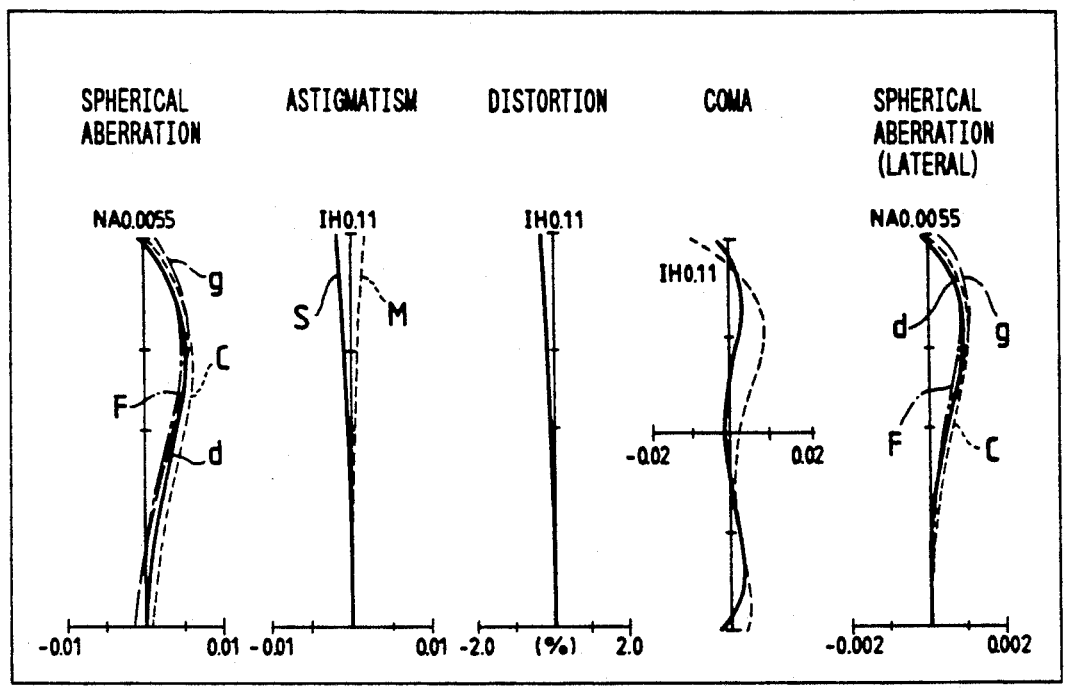

Aberration characteristics of the Embodiment 4 are visualized in FIG. 31 wherein spherical aberration is produced on the negative side, and aberration characteristics of the Embodiment 5 are illustrated in FIG. 32 wherein spherical aberration is produced on the positive side.

All of the Embodiments described above are designed so as to produce the maximum spherical aberration at aperture sizes of 0.65 to 7 normalized to the maximum aperture size 1.

Figure 26:
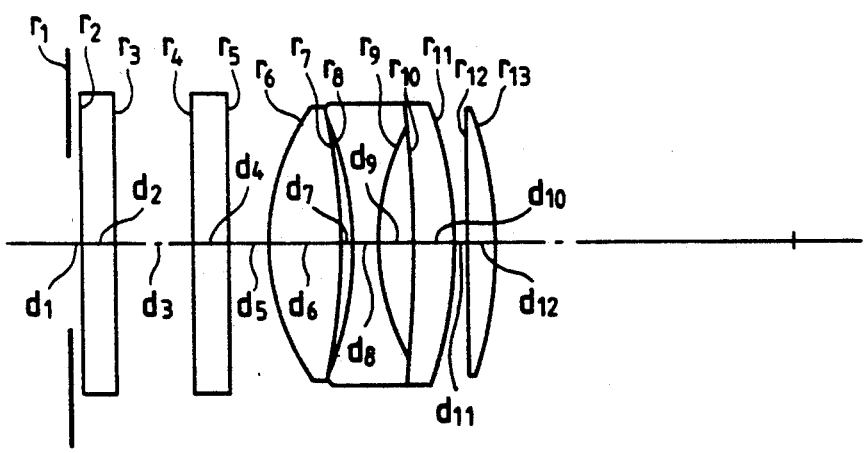
Figure 33:
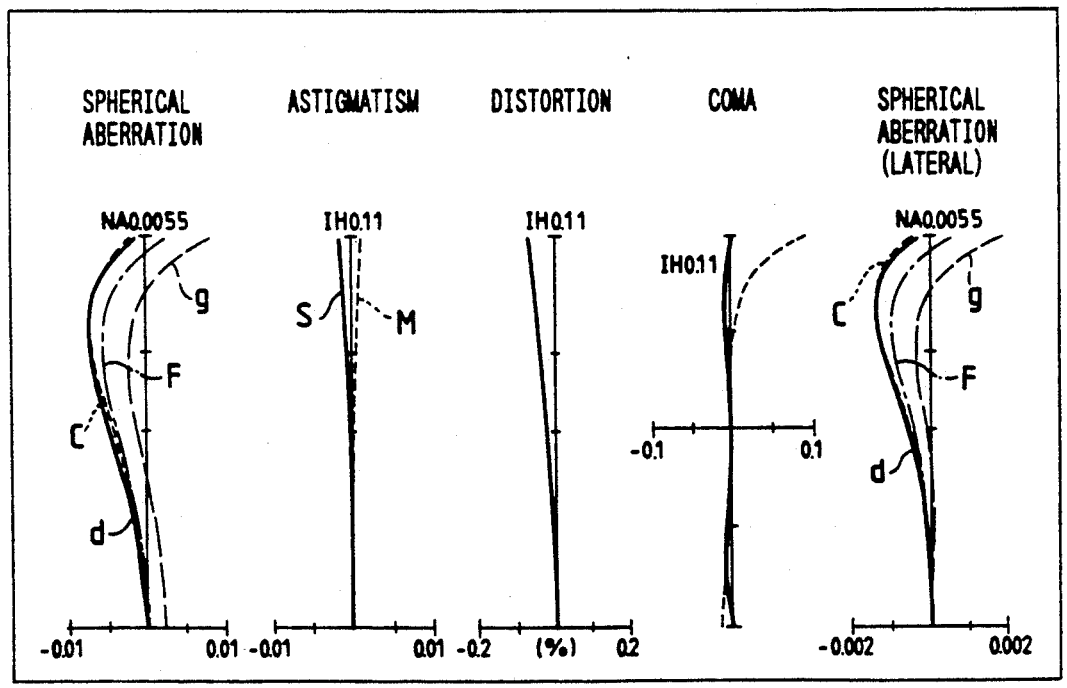

The Embodiment 7 has the composition shown in FIG. 26 and is composed only of spherical lens elements. The Embodiment 6 has the aberration characteristics illustrated in FIG. 33.

Figure 34:
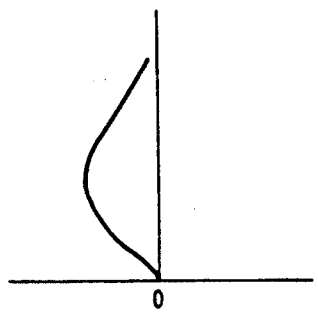
FIG. 34 through FIG. 36 show graphs exemplifying curves of the spherical aberration to be produced in the optical system according to the present invention.
Figure 35:
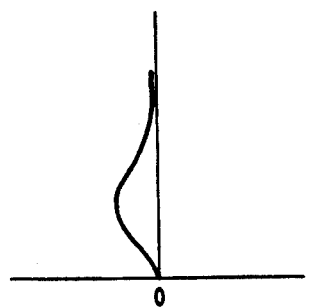
Figure 36:
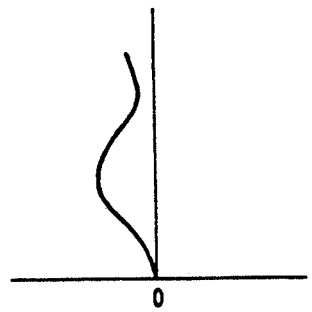

Though the Embodiments 1 through 6 described above are designed so as to produce spherical aberration in the maximum amounts at aperture size on the order of 0.7 normalized to the maximum aperture size 1, it is possible to modify the spherical aberration curves of these embodiments into the shape shown in FIG. 34 so that the spherical aberration will be maximum at smaller aperture sizes. When the imaging optical system according to the present invention is to be used with a fiber scope having a smaller aperture size. It is necessary to produce spherical aberration in the optical system at a smaller aperture size thereof. Further, it is allowable to produce spherical aberration of higher orders so as to modify the spherical aberration curves into that illustrated in FIG. 37 or FIG. 38.

Figure 19:
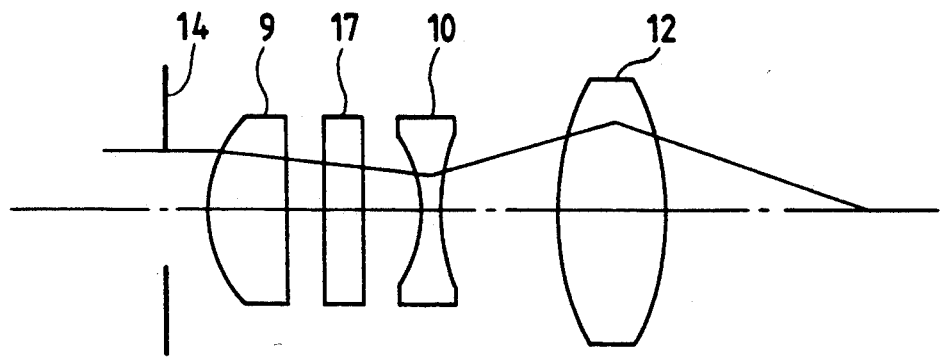
FIG. 19 shows a sectional view illustrating an example of a vari-focal optical system comprising a birefringent plate.
Figure 20:
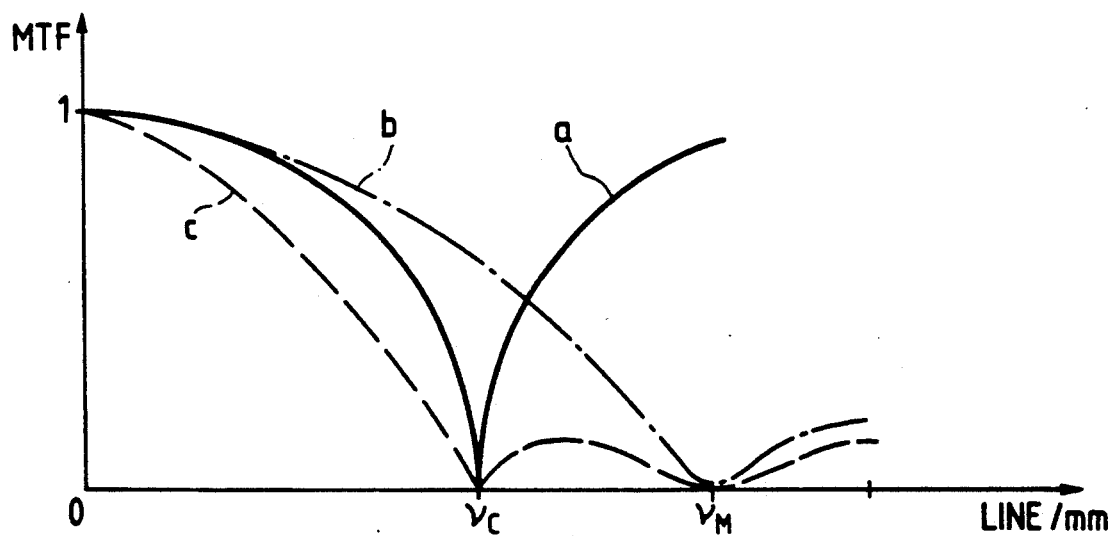
FIG. 20 shows graphs illustrating the MTF characteristic of the birefringent plate, an MTF characteristic of spherical aberration and an MTF characteristic of a combination thereof.
Figure 27A:
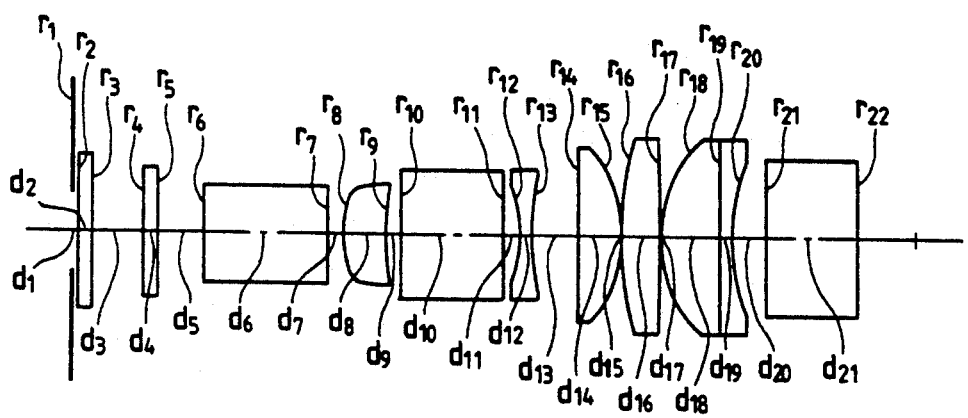
FIG. 27A and FIG. 27B show sectional views illustrating composition of Embodiment 7 of the present invention.
Figure 27B:
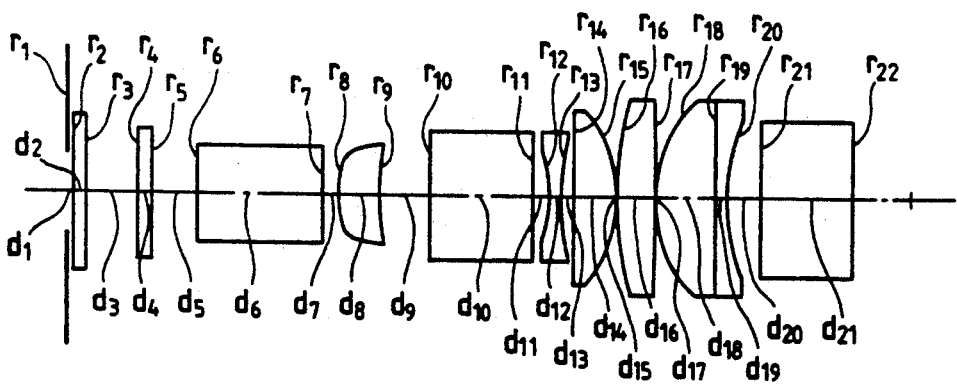

The Embodiment 7 has the composition illustrated in FIG. 27A and FIG. 27B, and is designed such a varifocal lens system as shown in FIG. 19.

Figure 37:
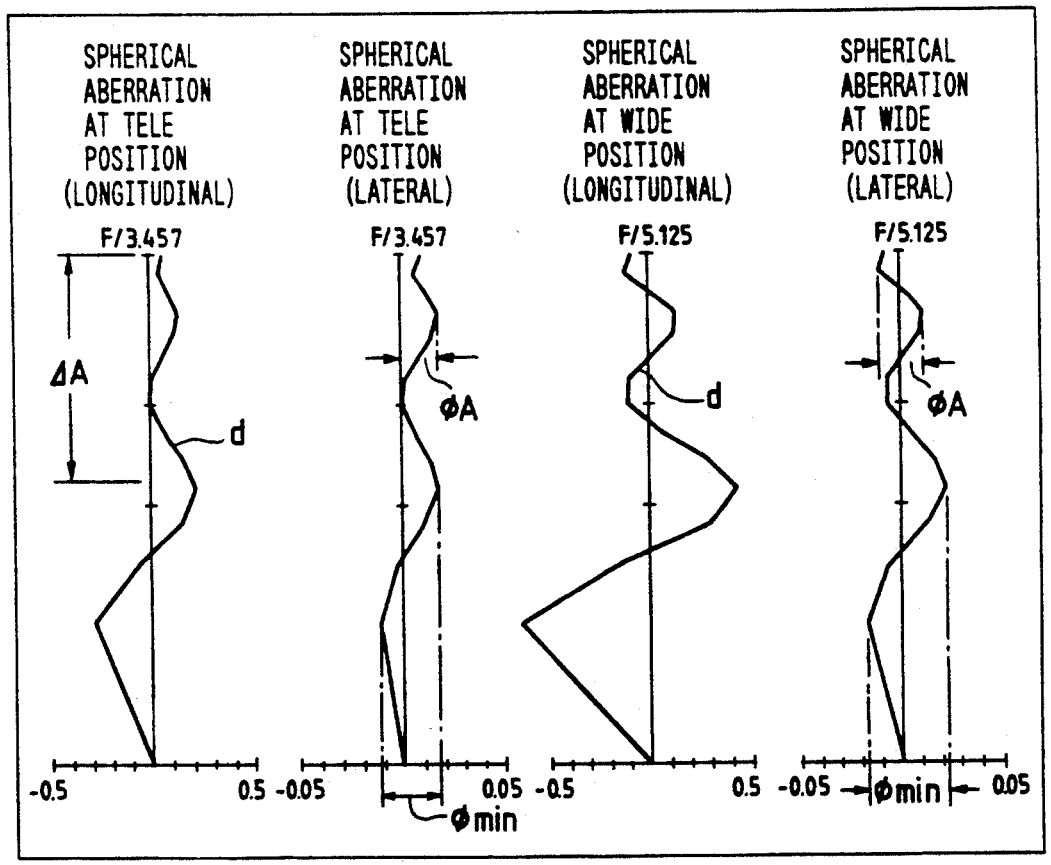
FIG. 37 shows curves illustrating aberration characteristics of the Embodiment 7 of the present invention.
Figure 38A:
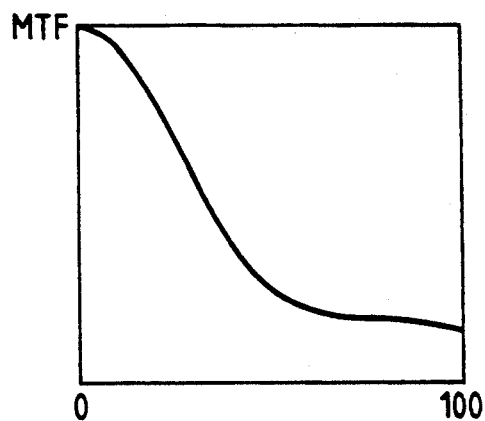
FIG. 38A, FIG. 38B, FIG. 38C, FIG. 38D, FIG. 39A and FIG. 39B show curves illustrating MTF characteristics of the Embodiment 7 of the present invention.
Figure 38B:
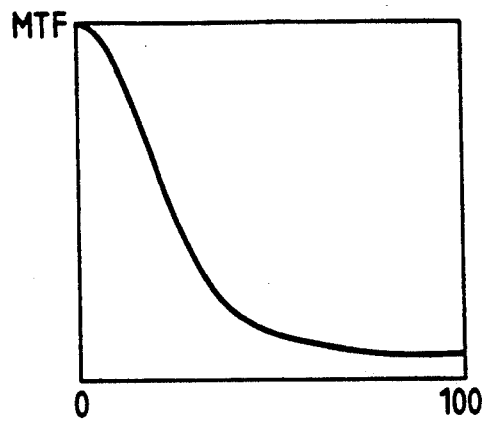
Figure 38C:
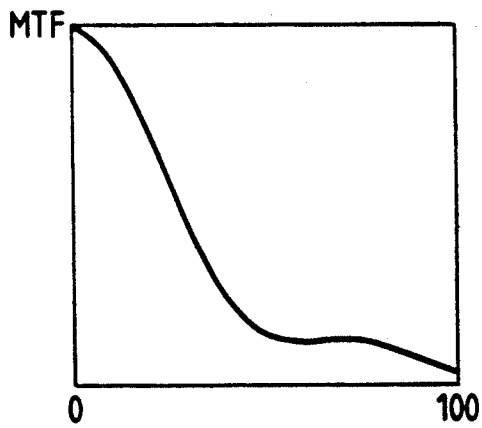
Figure 38D:
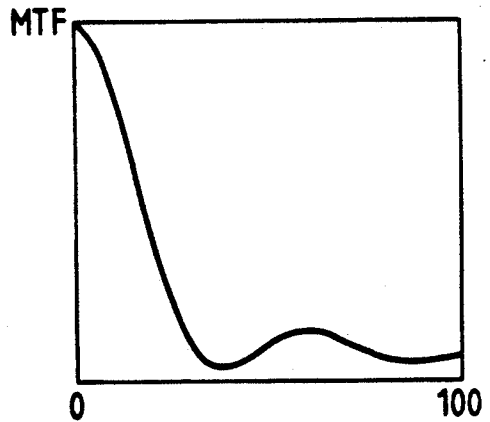

The Embodiment 7 produces spherical aberration as shown in FIG. 37, and has the values of $\phi_{min}$ and $\phi_A$ listed below:

At wide position: $\phi_{min} \approx 0.03$, $\phi_A \approx 0.0175$
At tele position: $\phi_{min} \approx 0.04$, $\phi_A \approx 0.02$ MTF's at the maximum aperture size at the wide position, at the maximum aperture size at the tele position, at the minimum aperture size at the wide position and at the minimum aperture size at the tele position of the Embodiment 7 are illustrated in FIG. 38A, FIG. 38B, FIG. 38C and FIG. 38D respectively. Since MTF is varied by varying aperture size and focal length as visualized by these drawings, MTF can be lowered by reducing aperture size and/or zooming from the wide position to the tele position as demanded by endoscopes combined with the Embodiment 7 of the imaging optical system according to the present invention.

In the Embodiment 7 described above, a quartz plate is arranged before the variator. This quartz plate is 2.587 mm thick and arranged so as to split a spot image into two in the direction coincident with the horizontal scanning direction on the CCD.

Figure 39A:
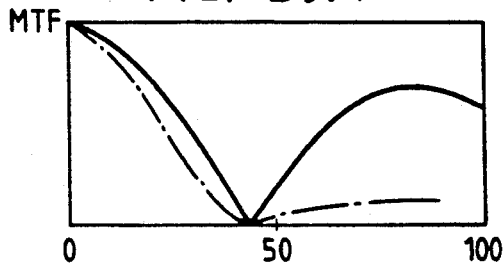
Figure 39B:
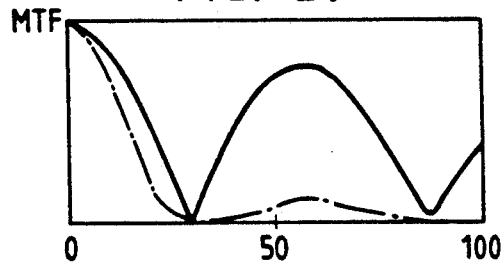

For the spot images split by the quartz plate used in the Embodiment 7, the rear lens unit (the lens components arranged on the image side of the quartz plate) has a magnification of ×0.7613 at the wide position and a magnification of ×1.1309 at the tele position. Accordingly, the MTF of the quartz plate is as indicated by the solid lines in FIG. 39A (at the wide position) and in FIG. 39B (at the tele position). However, the MTF's shown in these drawings include the influence due to the refraction by the aperture. Further, the dotted line shown in FIG. 39A indicates a product of the MTF of the quartz plate multiplied by the MTF of the spherical aberration at the maximum aperture size, whereas the dotted line shown in FIG. 39B indicates a product of the MTF of the quartz plate multiplied by the MTF of spherical aberration at the minimum aperture size.

As is clear from these drawings, the Embodiment 7 make use of the merit of the MTF of the quartz plate and that of the MTF of the spherical aberration, allows determining the cut-off frequency at the desired value without fail and permits suppressing the defect of the quartz plate that it enhances MTF thereof at the high frequencies.

The Embodiment 8 has the composition and numerical data which are same as those of the Embodiment 7, except for the shape of the aspherical surface which is different from that of the aspherical surface used in the Embodiment 7 and has the following aspherical surface coefficients.

Figure 40:
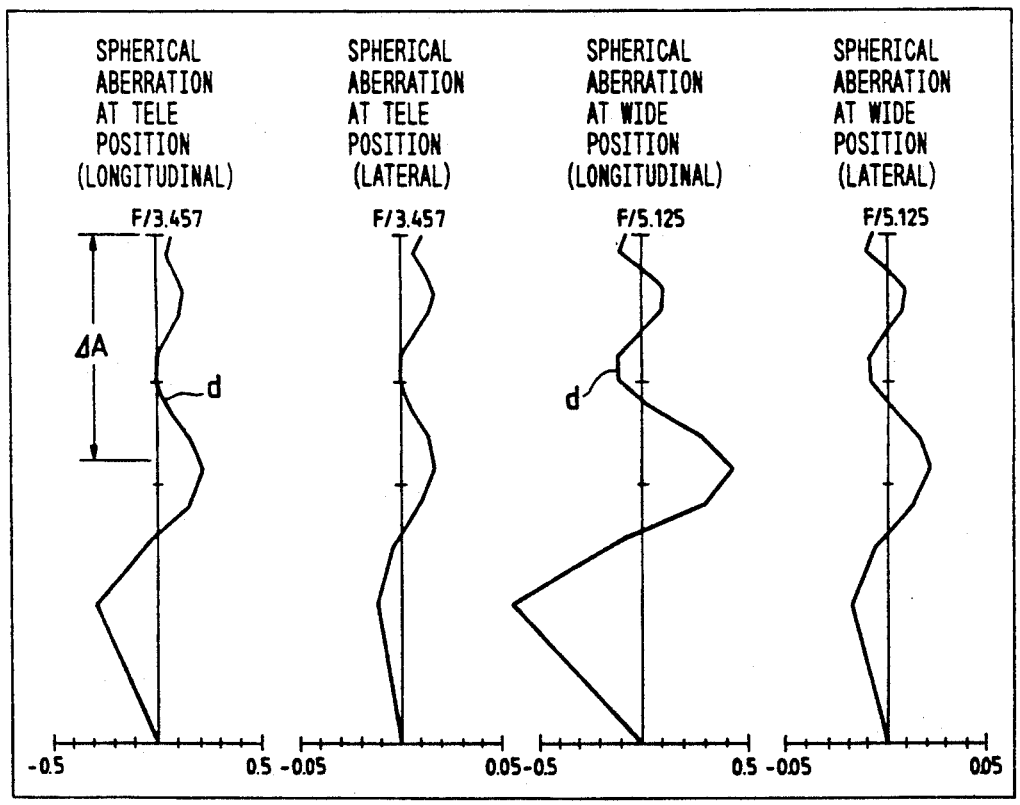
FIG. 40 shows graphs illustrating aberration characteristics of an Embodiment 8 of the present invention.
Figure 41A:
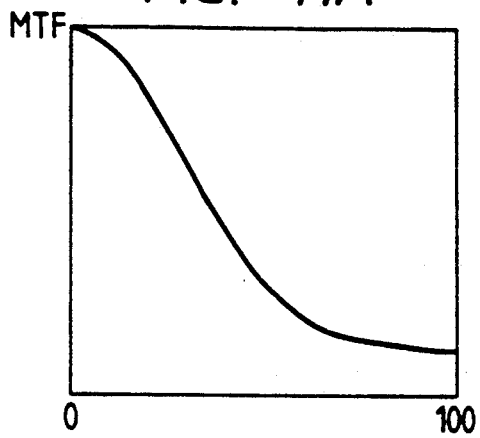
FIG. 41A, FIG. 41B, FIG. 41C, FIG. 41D, FIG. 42A, FIG. 42B, FIG. 42C, FIG. 42D, FIG. 43A and FIG. 43B show MTF characteristics of the Embodiemnt 8 of the present invention.
Figure 41B:
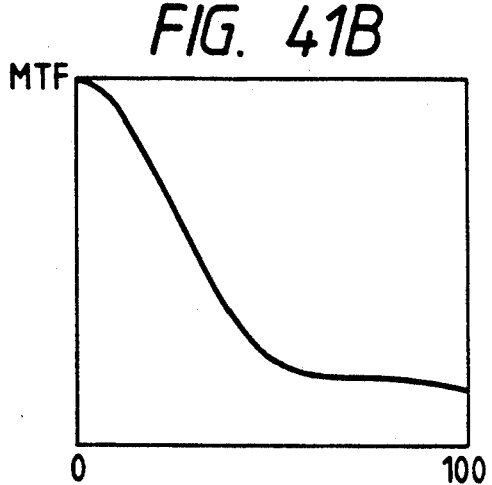
Figure 41C:
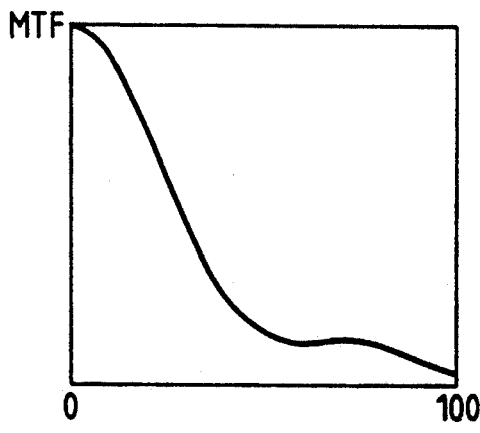
Figure 41D:
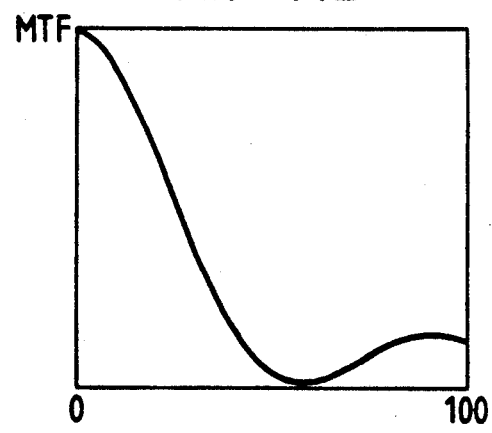
Figure 42A:
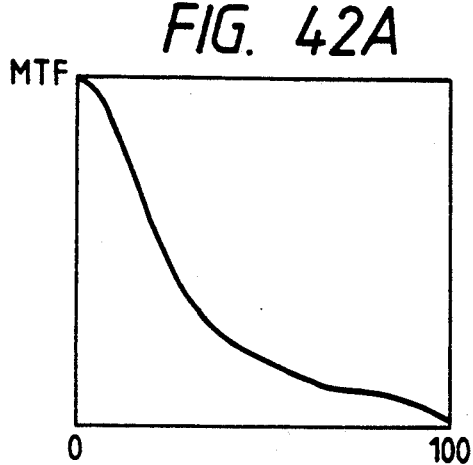
Figure 42B:
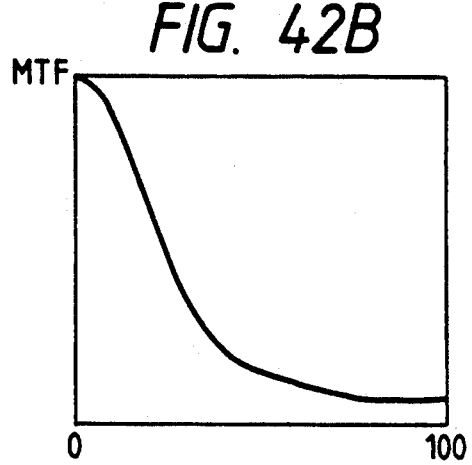
Figure 42C:
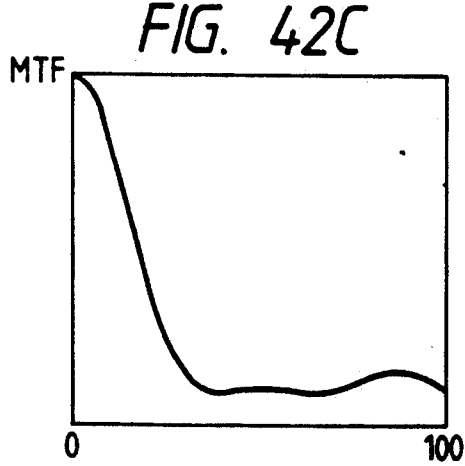
Figure 42D:
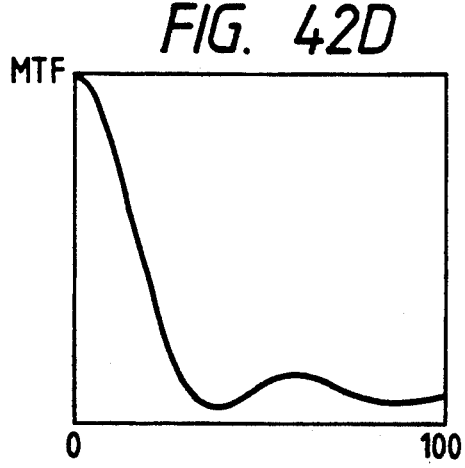

$P = 1.0000$, $E = 0.24049 \times 10^{-2}$, $B = 0$
$F = -0.28949 \times 10^{-2}$, $G = 0.13801 \times 10^{-2}$
$H = -0.33659 \times 10^{-3}$, $I = 0.44436 \times 10^{-4}$
$J = -0.30188 \times 10^{-5}$, $K = 0.82612 \times 10^{-7}$ ps Further, the Embodiment 8 produces spherical aberration as shown in FIG. 40, and has the values of $\phi_{min}$ and $\phi_A$ listed below:

At the wide position: $\phi_{min} \approx 0.03$, $\phi_A \approx 0.0165$
At the tele position: $\phi_{min} \approx 0.04$, $\phi_A \approx 0.02$ MTF's at the wide position of the Embodiment 8 are shown in FIG. 41A, FIG. 41B, FIG. 41C and FIG. 41D, whereas those at the tele position thereof are illustrated in FIG. 42A, FIG. 42B, FIG. 42C and FIG. 42D. FIG. 41A and FIG. 42A show the MTF's at the maximum aperture size with a defocused distance of 0.05 from the Gaussian image surface, FIG. 41B and FIG. 42B show the MTF's at the maximum aperture size with a defocused distance of 0.1 from the Gaussian image surface, FIG. 41C and FIG. 42C illustrate the MTF's at the minimum aperture size with a defocused distance of 0.05 from the Gaussian image surface, and FIG. 41D and FIG. 42D visualize the MTF's at the minimum aperture size with a defocused distance of 0.1 from the Gaussian image surface.

Figure 43A:
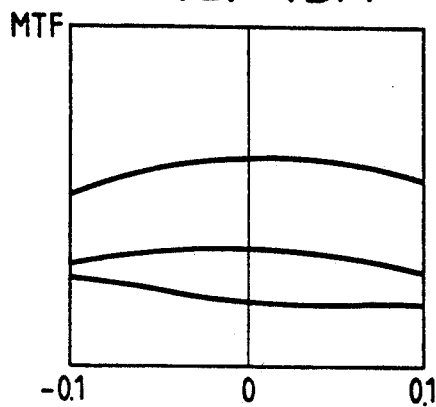
Figure 43B:
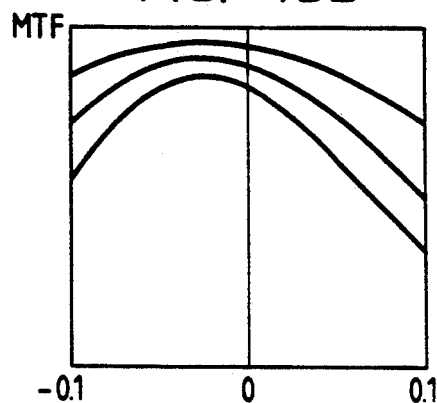
Figure 45A:
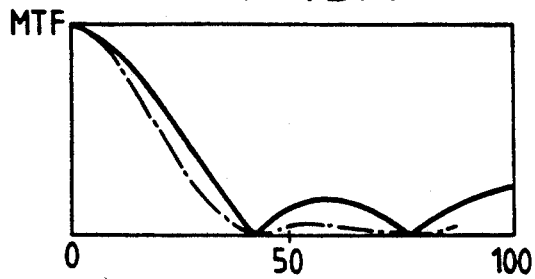
FIG. 45A and FIG. 45B show curves illustrating MTF characteristics of optical systems comprising quartz filters.

Though the defocused distances are the same between the wide position and the tele position, the central values are not located on the image surface. This is because the spherical aberration curves are inclined toward the positive side on the whole as seen from the spherical aberration curves at the wide position illustrated in FIG. 40, thereby shifting the best image surfaces more or less toward the positive side. The shift distances can be judged from FIG. 43A and FIG. 43B. FIG. 45A illustrates defocused distance versus values of MTF's of 20 lines/mm, 30 lines/mm and 40 lines/mm at the maximum aperture size at the tele position of the Embodiment 8. Further, FIG. 43B shows MTF's of an optical system which has the same paraxial design values as those of the Embodiment 7 or 8 and spherical aberration corrected to a certain degree (an optical system designed by selecting the aspherical surface coefficients of $P=1$ and $E$, $F$, ... $=0$ in the Embodiment 7 or 8). From these drawings, it will be understood that the Embodiment 8 has a stable MTF characteristic which is little varied by defocusing.

Figure 44A:
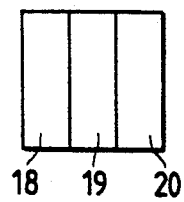
FIG. 44A, FIG. 44B and FIG. 44C show diagrams illustrating structure of a quartz filter.
Figure 44C:
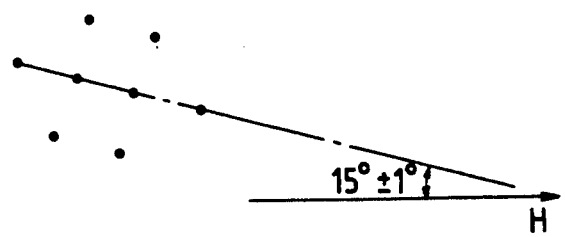
Figure 44B:
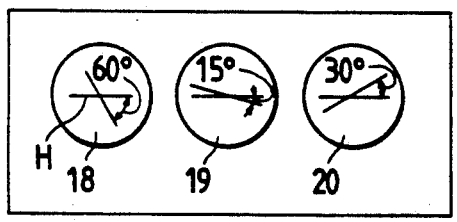

The Embodiment 8 uses an optical filter which is composed of three quartz plates as shown in FIG. 44A. The quartz plates 18, 19 and 20 comprising this optical filter split the ordinary ray and the extraordinary ray in the directions shown in FIG. 44C relative to the horizontal scanning direction H on the CCD, and have a function to split a single point into eight points. In case of an imaging optical system for endoscopes which is composed by combining a fiber scope with a CCD, the image guide is densely filled with optical fibers in a hexagonal sectional shape and it is desirable that the splitting direction of the quartz plates used in the imaging optical system has an inclination angle of 15° relative to the horizontal scanning direction on the CCD as shown in FIG. 44C.

Figure 45B:
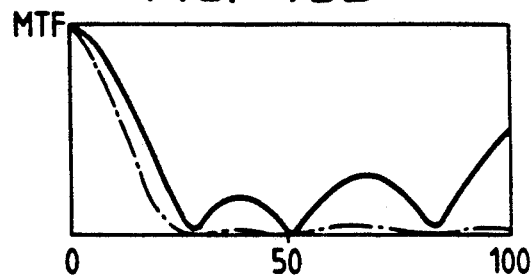

Use of the optical filter composed of the quartz plates as described above makes it possible to obtain the MTF characteristics as those indicated by the solid lines in FIG. 45A and FIG. 45B. Out of these drawings, FIG. 45A visualizes the MTF characteristic at the wide position and FIG. 45B shows the MTF characteristic at the tele position which are traced in the direction of the horizontal scanning direction on the CCD (the direction H). The chain lines in these drawings indicate the products of these MTF's multiplied by the MTF of the spherical abberation. In addition, the graphs shown in FIG. 45A and FIG. 45B correspond to the MTF characteristics at the maximum aperture size and the minimum aperture size respectively.

Though the quartz plates are arranged before the variator in the Embodiments 7 and 8, the optical low pass filter may be arranged right before the CCD. Further, though the optical low pass filters are designed separately from the lens elements in the Embodiments 7 and 8, it is possible to make any lens elements of a birefringent substance such as quartz so that the lens element has the function of the low pass filters. In such cases, the objects of the present invention can be accomplished by selecting the positional relationship between the lens elements made of the birefringent substance and the variator which is the same as that between the quartz plate and the variator selected for the Embodiment 8.

Not only the aspherical surface but also a graded refractive index lens is usable as the means for producing the spherical aberration of high orders. Further, the aspherical surface can be used on a lens element, but on a half prism or a cover glass.

Figure 46:
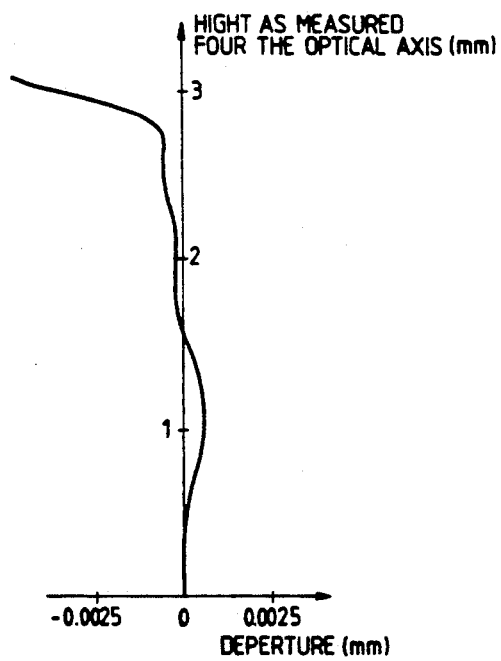
FIG. 46 shows a curve exemplifying a shape of an aspherical surface to be used in the imaging optical system according to the present invention.

The Embodiments 7 and 8 use the aspherical surfaces as the means for producing the spherical aberration of high orders for accomplishing the objects of the present invention. The aspherical surfaces have such a shape as shown in FIG. 46. This drawing shows degrees of deviations from the spherical surface which is used as a standard for the aspherical surfaces used in these embodiments (referred to as the reference sphere). In this drawing, height as measured from the optical axis is taken as the ordinate and the departure from the reference sphere is taken as the abscissa.

The Embodiment 9 has the composition which is the same as that of the Embodiment 7 but adopts an aspherical surface having a shape different from that of the aspherical surface used in the Embodiment 7. In other words, the Embodiment 9 has the numerical data which are the same as those of the Embodiment 7 but selects the following values for the aspherical surface coefficients which are different from those used for the Embodiment 7:

$P = 0.8818$, $B = 0$, $E = -0.24049 \times 10^{-1}$
$F = 0.28949 \times 10^{-2}$, $G = -0.13801 \times 10^{-2}$
$H = 0.33659 \times 10^{-3}$, $I = -0.44436 \times 10^{-4}$
$J = 0.30188 \times 10^{-5}$, $K = -0.82612 \times 10^{-7}$ The aspherical surface having the values listed above of the aspherical surface coefficients has departure from the reference sphere in the direction opposite to that of the aspherical surface used in the Embodiment 7.

Figure 49:
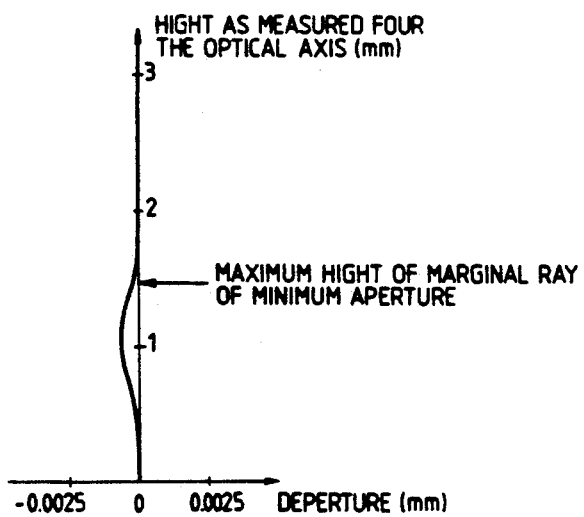
FIG. 49 shows a curve illustrating a shape of an aspherical surface to be used in the Embodiment 10 of the present invention.

The shape of the aspherical surface used in the Embodiment 9 is illustrated in FIG. 49. Aberration characteristics of the Embodiment 9 are visualized in FIG. 50.

Figure 47:
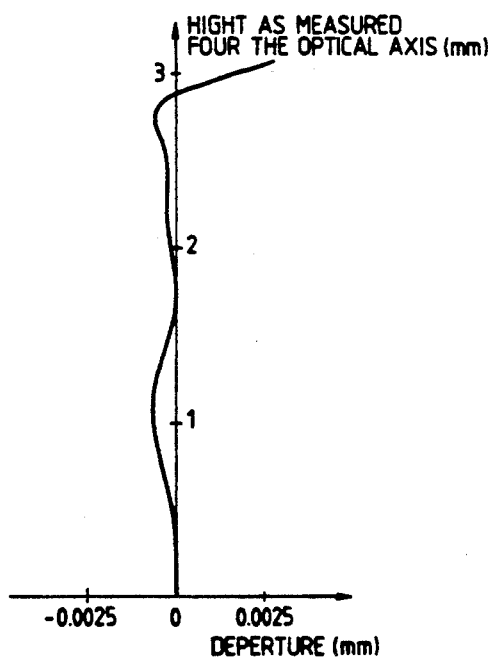
FIG. 47 shows a curve illustrating a shape of an aspherical surface to be used in the Embodiment 9 of the present invention.
Figure 48:
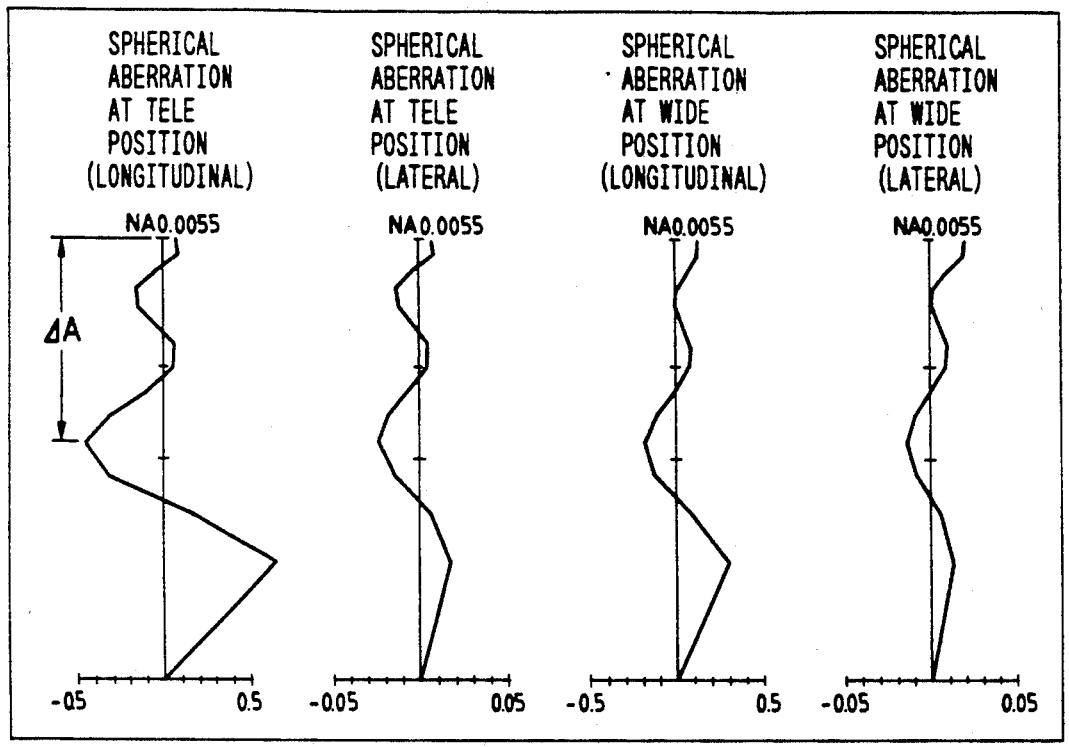
FIG. 48 shows curves illustrating aberration characteristics of the Embodiment 9 of the present invention.

The Embodiment 10 has the composition and the values of the parameters which are the same as those of the Embodiment 7. However, the aspherical surface used in the Embodiment 9 has a departure of 0 from the reference sphere thereof as shown in FIG. 49 at the portions of the shape of the aspherical surface shown in FIG. 47 which are located above the ray which is the highest at the minimum aperture size.

Figure 50:
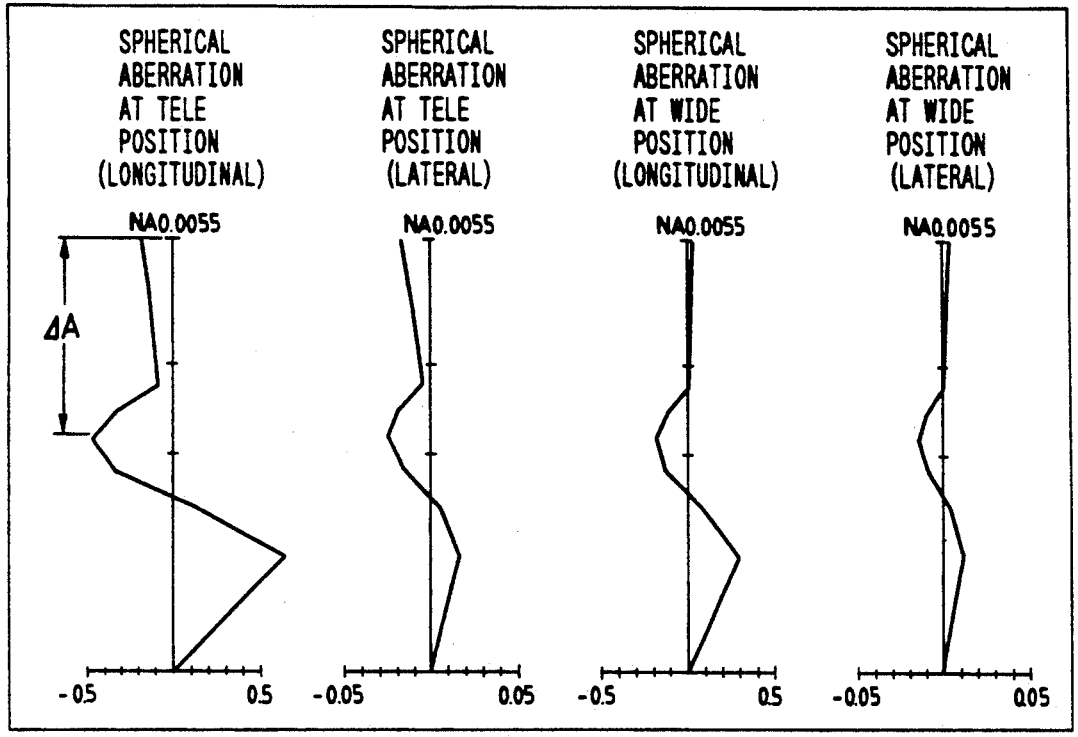
FIG. 50 shows curves illustrating aberration characteristics of an Embodiment 10 of the present invention.

Aberration characteristics of the Embodiment 10 are visualized in FIG. 50.

In addition, the shapes of the aspherical surfaces are illustrated in terms of departures from the reference spheres.

Since spherical aberration is favorably corrected in the optical systems described above as the preferred embodiments when the optical systems uses the reference spheres in place of the aspherical surfaces, the curves obtained as the first derivatives of the departures from the reference spheres are close to the spherical aberration curves. That is to say, the aspherical surface to be used in the imaging optical system according to the present invention must have a shape having at least one inflection point at aperture sizes smaller than the minimum aperture size.

That is to say, the departure from the reference sphere must have at least one inflection point at aperture sizes smaller than the minimum aperture size and another inflection point within the range wherein aperture size varies. In other words, the departure from the reference sphere must have at least two inflection points.

Further, from the viewpoints of chemical resistance of the aspherical lens element when used in endoscopes, manufacturing convenience of the aspherical lens element and reduction of manufacturing cost of the imaging optical system, it is desirable to manufacture the aspherical lens element to be used in the imaging optical system according to the present invention by molding an optical glass material, but plastic materials may be selected as occasion demands.

Figure 51:
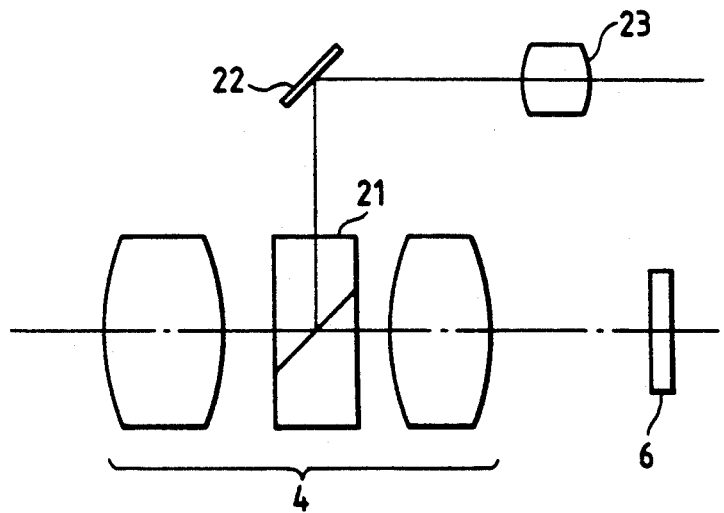
FIG. 51 shows a schematic sectional view illustrating a composition of a single reflex type television camera using the imaging optical system according to the present invention.

In addition, when the imaging optical system according to the present invention is to be used in a television camera equipped with a single-lens reflex type television camera, a half prism 11 is arranged in the imaging optical system 4 as shown in FIG. 51 for splitting light into a finder optical path and leading the light reflected by the half prism to an eyepiece lens 13 by way of a reflecting mirror 12. In this case, it is desirable to arrange the above-mentioned aspherical surface on the image side of the prism 11 so that the aspherical surface will not give influence on an image observed through the finder system.

We claim:

1. An imaging optical system comprising:

an imaging lens means for forming images of objects; and a spatial filtering optical means for limiting spatial frequency response of said imaging optical system;

wherein said spatial filtering means includes an optical element having, as a refractive surface, an aspherical surface so that a light bundle having a smaller height of incidence thereon than a light bundle having a larger height of incidence produces larger quantities of axially symmetrical aberrations, whereby said imaging optical system exhibits a lower spatial frequency response to the light bundle having a smaller height of incidence than to the light bundle having a larger height of incidence.

2. An imaging apparatus comprising:

an imaging lens means for forming images of objects; and an electronic image pickup means for receiving said images of objects;

wherein said imaging lens means includes an optical element having, as a refracting surface, an aspherical surface so that a light bundle having a smaller height of incidence thereon than a light bundle having a larger height of incidence produces larger quantities of axially symmetrical aberrations, whereby said imaging apparatus exhibits a lower spatial frequency response to the light bundle having a smaller height of incidence than to the light bundle having a larger height of incidence; and wherein said imaging apparatus has an effect that differs for light bundles having different thicknesses, to eliminate moiré that is produced at a stage to reimage said images of objects onto an image receiving surface of said electronic image pickup means.

3. An imaging system for endoscopes comprising;

a fiberscope including an objective lens for forming images of objects, an image guide fiber bundle for receiving the images formed by said objective lens on an end surface of incidence thereof and transmitting said images to an end surface of emergence thereof, an eyepiece lens through which images appearing on the end surface of emergence are observed, and an electronic image pickup unit including an imaging lens means and an electronic image pickup means, said electronic image pickup unit being disposed after the eyepiece lens of said fiberscope for picking up images appearing on the end surface of emergence of said image guide fiber bundle;

wherein said imaging lens means includes as a refracting surface, an aspherical surface, so that a light bundle having a smaller height of incidence thereon than a light bundle having a larger height of incidence produces larger quantities of axially symmetrical aberrations, whereby said imaging system exhibits, on an image receiving surface of said electronic image pickup means, a lower spatial frequency response to the light bundle having a smaller height of incidence than to the light bundle having a larger height of incidence; and wherein said imaging system operates to eliminate unwanted moiré produced at a stage to reimage said images appearing on the end surface of emergence of said image guide fiber bundle onto an image receiving surface of said electronic image pickup means.

4. An invention according to claim 1, 2 or 3 wherein said aspherical surface satisfies the following condition:

$$1 \times 10^{-5} < |\Delta z|/f < 5 \times 10^{-2} \quad (1)$$

wherein the reference symbol $\Delta z$ represents departure from a reference sphere at a height of a marginal ray passing through said aspherical surface at a maximum aperture size, and the reference symbol f designates focal length of the imaging optical system as a whole.

5. An invention according to claim 1, 2 or 3 wherein departure from a reference sphere of said aspherical surface has at least one inflection point between a maximum value and a minimum value of heights of incidence of light bundles incident on said imaging lens means.

6. An imagine optical system according to claim 1 wherein said imaging lens means is a vari-focal lens system and said spatial filtering optical means is disposed on an object side of a lens component contributing to variation of focal length.

7. An imaging apparatus according to claim 2 further comprising an optical low pass filter including at least a birefringent plate, said optical low pass filter having a cutoff frequency for spatial frequency response lower than the cutoff frequency for spatial frequency response of said imaging lens means.

8. An imaging apparatus according to claim 2 further comprising a light splitting means disposed in an optical path for leading a light bundle incident on said imaging lens means to the image surface of said electronic image pickup means; and a finder optical system disposed in the optical path being branched by said light splitting means; and wherein said finder optical system is disposed on an image side of said light splitting means.

9. An imaging apparatus according to claim 2 wherein the light bundle having the smaller height of incidence on said imaging lens means is higher on the image receiving surface of said electronic image pickup means than the light bundle having the larger height of incidence on said imaging lens means.

10. An imaging system for endoscopes according to claim 3 wherein the light bundle having the smaller height of incidence on said imaging lens means is higher on the image receiving surface of said electronic image pickup means than the light bundle having the larger height of incidence on said imaging lens means.

11. An invention according to claim 5 wherein said aspherical surface has, in the departure from the reference sphere thereof, an inflection point at a position lower than said minimum value.

* * * * *